United States Patent
Kanda et al.

(10) Patent No.: US 7,198,601 B2
(45) Date of Patent: Apr. 3, 2007

(54) ULTRASONIC CONTRAST MEDIUM IMAGING APPARATUS AND METHOD

(75) Inventors: Hiroshi Kanda, Saitama (JP); Tatsuya Hayashi, Chiba (JP); Tsuyoshi Mitake, Chiba (JP); Minoru Yoshida, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 402 days.

(21) Appl. No.: 10/392,612

(22) PCT Filed: Feb. 1, 2002

(86) PCT No.: PCT/JP02/00839

§ 371 (c)(1),
(2), (4) Date: Jul. 11, 2003

(87) PCT Pub. No.: WO02/060326

PCT Pub. Date: Aug. 8, 2002

(65) Prior Publication Data

US 2004/0059218 A1    Mar. 25, 2004

(30) Foreign Application Priority Data

Feb. 1, 2001  (JP)  ............................. 2001-025778
Feb. 1, 2001  (JP)  ............................. 2001-025783

(51) Int. Cl.
*A61B 8/00*  (2006.01)
(52) U.S. Cl. .................................................... 600/458
(58) Field of Classification Search ........ 600/440–441, 600/443, 447, 458; 128/916
See application file for complete search history.

(56) References Cited

U.S. PATENT DOCUMENTS

| | | | | |
|---|---|---|---|---|
| 5,749,364 A * | 5/1998 | Sliwa et al. | ................. | 600/438 |
| 5,879,303 A | 3/1999 | Averkiou | | |
| 6,132,377 A * | 10/2000 | Bolorforosh et al. | ....... | 600/458 |
| 6,146,330 A | 11/2000 | Tujino | | |
| 6,290,647 B1 * | 9/2001 | Krishnan | ..................... | 600/441 |
| 6,413,221 B1 * | 7/2002 | Brock-Fisher | .............. | 600/458 |
| 6,458,083 B1 * | 10/2002 | Jago et al. | .................. | 600/443 |
| 6,461,303 B2 * | 10/2002 | Angelsen | .................... | 600/458 |
| 6,497,666 B1 * | 12/2002 | Phillips et al. | .............. | 600/458 |
| 6,508,767 B2 * | 1/2003 | Burns et al. | ................. | 600/443 |
| 6,514,206 B2 * | 2/2003 | Maxwell et al. | ............ | 600/443 |
| 6,516,667 B1 * | 2/2003 | Broad et al. | .................. | 73/602 |
| 6,626,836 B2 * | 9/2003 | Mao et al. | .................. | 600/455 |
| 6,656,123 B2 * | 12/2003 | Jensen et al. | ............... | 600/458 |
| 6,929,609 B2 * | 8/2005 | Asafusa | ...................... | 600/439 |

FOREIGN PATENT DOCUMENTS

EP        0 770 352        5/1997

* cited by examiner

*Primary Examiner*—Francis J. Jaworski
(74) *Attorney, Agent, or Firm*—Antonelli, Terry, Stout and Kraus, LLP.

(57) ABSTRACT

An ultrasonic enhanced-contrast imager includes an ultrasonic probe for transmitting an ultrasonic wave to an organism and receiving an ultrasonic wave from the organism, a transmitting section for transmitting an ultrasonic signal to the ultrasonic probe, a receiving section for processing a response signal ultrasonic wave received by the ultrasonic probe, a filter for extracting a specific frequency component from the processed response signal, a setting control section for setting a pass frequency band of the filter on the basis of a frequency band of the response signal from a contrast medium injected to the organism, and a control section for controlling the operation of the filter in the set pass band.

62 Claims, 7 Drawing Sheets

ULTRASONIC CONTRAST MEDIUM IMAGING APPARATUS AND METHOD

TECHNICAL FIELD

The present invention relates to an ultrasonic enhanced-contrast imager for obtaining imaging information required in the diagnosis of blood flow distribution, etc. by using an ultrasonic contrast medium, and its method; and, more particularly, the invention relates to a technique for attenuating a higher harmonic wave component included in a response signal from organic tissue, thereby making it possible to clearly image the distribution of the contrast medium.

BACKGROUND OF THE INVENTION

An ultrasonic enhanced-contrast imaging method and device using an ultrasonic contrast medium are often used for measuring the blood flow within tissue. An example of such an imaging method and device are described in "Ultrasound Contrast Imaging: Current and New Potential Methods: Peter J. A. Frinking et al." in "Ultrasound in Medicine & Biology", Vol. 26, No. 6, p. 965, 2000.

The ultrasonic contrast medium is generally formed by mixing many air bubbles into a liquid medium, such as a physiological salt solution, etc. For example, the ultrasonic contrast medium is formed by covering an inert gas ($C_3F_8$, $C_4F_{10}$) with a protein film or a fat film and is generally formed in a spherical shape. The particle diameter distribution of the ultrasonic contrast medium is generally set to a Gaussian normal distribution, and the average particle diameter is several μm. However, in air bubbles of 0.5 μm or less, the air bubbles gather, and become substantially larger diameter particles, so that the normal distribution is slightly distorted.

Such a contrast medium is generally injected through a vein into the organism. When an ultrasonic beam is irradiated to a contrast medium that has been injected into the organism and its sound pressure is low, the contrast medium is deformed, and acoustic information created by this deformation is reflected and emitted from the contrast medium as a response signal of the ultrasonic wave. In contrast to this, when the sound pressure is high, the contrast medium is destroyed, and a strong response signal is emitted from the contrast medium due to this destruction. In each case, the ultrasonic contrast medium exhibits a nonlinear response to the ultrasonic wave. When the ultrasonic wave, whose fundamental frequency component is $f_0$, is irradiated, the signal of a higher harmonic wave component $2f_0$ is included in the response signal, in addition to the signal corresponding to the fundamental frequency component $f_0$.

Such behavior of the contrast medium as deformation and destruction is generally divided into an initial time phase and a latter time phase, depending on the time that has passed since the injection of the contrast medium through the vein. The initial time phase is the time phase in which the ultrasonic contrast medium injected through the vein flows by blood circulation into the tissue, such as the liver, etc., which represents the diagnostic object. The latter time phase is a time phase in which it is anticipated that the ultrasonic contrast medium that has flowed and been distributed into the tissue is has now sufficiently flowed in reverse out of the tissue with the blood circulation after 2 to 8 minutes have passed after the injection of the contrast medium through the vein. In the initial time phase, an ultrasonic sound pressure (e.g., MI: mechanical index=0.2) for generating a sufficiently higher harmonic wave, without destroying the contrast medium, is generally used. When the higher harmonic wave component $2f_0$ included in the response signal from the contrast medium is detected, it is possible to grasp the distribution and flow of the contrast medium in the tissue and blood vessels. In the latter time phase, the contrast medium will have almost all flowed out of the tissue, but one portion of the contrast medium is trapped within the tissue. A diseased portion and a healthy normal portion of the tissue differ as to whether the contrast medium is trapped in the tissue or not. When an ultrasonic wave having a high ultrasonic sound pressure (e.g., it is said that MI is about 0.8 or more) capable of destroying the contrast medium is irradiated in this latter time phase, a strong reflection signal is generated in the course of destruction of the contrast medium. Accordingly, it is possible to discriminate the area where the contrast medium is trapped, i.e., the diseased portion and the area where the contrast medium was not trapped, i.e., the healthy normal portion, by detecting the higher harmonic wave component $2f_0$ included in the response signal from the contrast medium.

The ultrasonic enhanced-contrast imager is a device for detecting the higher harmonic wave component $2f_0$ included in the response signal from the contrast medium and then imaging the blood flow distribution and the diseased portion within the tissue based on the position of the contrast medium. Therefore, the $2f_0$ component is conventionally extracted, and the existence of the contrast medium is detected by using a relatively narrow band pass filter (e.g., $1.8f_0$ to $2.2f_0$) having $2f_0$ as a central frequency. Namely, since the existence of the $2f_0$ component corresponds to the existence of the contrast medium, the largeness and smallness of the $2f_0$ component indicates the spatial density distribution or the destruction of the contrast medium. Accordingly, it is possible to detect into which part of the tissue the contrast medium has flowed, and in which part the contrast medium is trapped. In this case, since the frequency band is narrow, there arises the problem that the depth resolution is deteriorated.

In contrast to this, methods for extracting the higher harmonic wave by utilizing a non-linearity with respect to the frequency of the contrast medium response signal, without using a band pass filter, have been proposed in U.S. Pat. Nos. 5,632,277 and 5,706,819. In accordance with these methods, an ultrasonic pulse based on a first ultrasonic signal is irradiated into the organism, and its response signal is received. Then, an ultrasonic pulse based on a second ultrasonic signal obtained by inverting the polarity of the first ultrasonic signal is irradiated in the same ultrasonic beam direction at a short time interval, and its response signal is received. The component corresponding to the fundamental wave frequency $f_0$ within the response signal from the contrast medium is effectively removed by adding these received signals, and the higher harmonic wave component $2f_0$ is emphasized. Thus, the contrast medium can be detected with high depth resolution without using a band pass filter.

Further, JP-A-2000-300554 proposes a method wherein a first ultrasonic signal has a waveform in which a period $t_1$ providing a signal level of a positive constant value and a period $t_2$ providing a signal level of a negative constant value are repeated, and a second ultrasonic signal has a waveform obtained by inverting this first ultrasonic signal with respect to the time axis. In accordance with this construction, the symmetry of an ultrasonic pulse based on the first and second ultrasonic signals is raised, and the signal of a fundamental wave component (linear component) can be lessened.

Each of these conventional techniques is effective to extract or emphasize the higher harmonic wave component $2f_0$ caused by the contrast medium. However, no consideration has been given to the case in which the higher harmonic wave component $2f_0$, that is included in the response signal from the tissue, is large to such an extent that this higher harmonic wave component $2f_0$ cannot be neglected in verification of the higher harmonic wave component included in the response signal of the contrast medium. Therefore, there are cases in which the higher harmonic wave component included in the response signal of the contrast medium can not be effectively extracted, such as where the tissue is relatively deep beneath the body surface.

Namely, a nonlinear phenomenon, which here is the key to contrast medium detection, is also caused by propagating the ultrasonic wave within the tissue in addition to the contrast medium. In this case, the higher harmonic wave component $2f_0$, having a frequency twice the fundamental frequency $f_0$ of the irradiated ultrasonic wave, is also generated. In particular, the strength of the signal of the higher harmonic wave component $2f_0$ included in the response signal from the tissue is increased as the depth is deepened, i.e., as the propagation length of the ultrasonic wave is increased. Therefore, when the higher harmonic wave component $2f_0$ of the tissue response signal is equivalent to or larger than the higher harmonic wave component $2f_0$ included in the response signal of the contrast medium, the higher harmonic wave component $2f_0$ of the tissue response signal prevents the detection of the contrast medium.

For example, the higher harmonic wave component of $2f_0$ is emitted from both the contrast medium within the blood vessel buried into the tissue, such as in a blood vessel within the liver, and from the tissue, during the detection of the contrast medium. Therefore, there is a fear that the existence of the contrast medium will be erroneously detected. Namely, in the conventional technique for emphasizing the higher harmonic wave component of $2f_0$, the $2f_0$ component included in the response signal from the contrast medium can not always be discriminated from the higher harmonic wave component $2f_0$ from the organic tissue. Accordingly, there is a case in which the detecting accuracy of the higher harmonic wave component of the contrast medium is reduced, and the definition of an enhanced-contrast image cannot be improved.

FIGS. 2A and 2B are graphs which shows the result of a detailed examination of the nonlinear response of the contrast medium and the tissue with respect to the ultrasonic irradiation of the fundamental frequency $2f_0$. These graphs typically show a frequency spectrum of the reflection response signal when the ultrasonic wave of the fundamental wave component $f_0$ is irradiated to the contrast medium distributed into the tissue. The axis of abscissa shows a frequency normalized at the fundamental wave $f_0$, and the axis of ordinate shows the signal strength of each frequency component. FIG. 2A shows the response signal from a relatively shallow part near a probe. FIG. 2B shows the response signal from a relatively deep part far from the probe. As can be seen from these figures, in both the shallow and deep parts, the response signal 1 of the contrast medium continuously includes the higher harmonic wave component over a wide frequency band, in addition to the fundamental wave component corresponding to the fundamental frequency $f_0$. In contrast to this, the response signal 2 from the tissue is divided into a fundamental wave component $2a$ of the fundamental wave frequency $f_0$ and a higher harmonic wave component $2b$ of the double higher harmonic wave $2f_0$. The higher harmonic wave component $2b$ is not so strong in the case of the shallow part, but it is very strong in the case of the deep part, and it is stronger than the response signal 1 of the contrast medium near the double higher harmonic wave $2f_0$. This is because the higher harmonic wave component $2b$ included in the response signal from the tissue is caused by the nonlinear effect in the propagation of the ultrasonic wave within the tissue as mentioned above, so that the propagation length is increased toward the deep part separated from the probe. Accordingly, even when the double higher harmonic wave component $2f_0$ is uniformly extracted and the response signal from the contrast medium is emphasized, as in the conventional method, the higher harmonic wave component $2f_0$ of the tissue is also emphasized as well, except at shallow positions, so that the definition of a enhanced-contrast image cannot be improved.

Therefore, an object of the present invention is to distinguish the higher harmonic wave component included in the response signal from the contrast medium from the higher harmonic wave component included in the response signal from the tissue, and to improve the definition of the enhanced-contrast image.

SUMMARY OF THE INVENTION

To achieve the above-stated object, matters relating to the characteristics of the ultrasonic enhanced-contrast imager of the present invention, as derived from the consideration of FIGS. 2A and 2B, will be presented as follows.

(1) The frequency spectrum of the response signal of the contrast medium does not localize at $2f_0$, but is distributed in a wide band. The fundamental wave component of the response signal of the contrast medium is not inferior to the fundamental wave component of the response signal of the tissue, but rather is stronger. The higher harmonic wave of the response signal of the tissue is very weak in comparison with the higher harmonic wave component of the contrast medium in the case of a relatively low ultrasonic sound pressure and in shallow tissue. These features suggest that it is not necessary to limit the response signal being detected to the double higher harmonic wave component $2f_0$ to extract the response signal from the contrast medium. Simultaneously, the contribution of the higher harmonic wave component included in the response signal of the tissue is not uniform in accordance with the deepness and shallowness of the part of the contrast medium being detected and the largeness and smallness of the irradiated ultrasonic sound pressure. Accordingly, in accordance with the present invention, the response signal from the contrast medium is detected over a wide band by varying the band width of the band pass filter in accordance with the size of the double higher harmonic wave component from the organic tissue, so that the definition of a contrast medium image is improved (first feature of the present invention).

(2) The above-mentioned wide band distribution is more notable as the frequency spectrum of the transmitted ultrasonic signal becomes wider. The response signal of the contrast medium strongly depends on the particle diameter of the contrast medium, and it is greatly emphasized at a free resonance frequency $f_R$ of the contrast medium. However, since the contrast medium has a particle diameter distribution, response signals from more of the contrast media particles within the whole particle diameter distribution can be expected when the ultrasonic wave over a wide band is irradiated (second feature of the present invention).

(3) The higher harmonic wave included in the response signal of the organic tissue is comparatively localized near $2f_0$ irrespective of the strength of the ultrasonic sound pressure. This is because the nonlinear response of the tissue and of the contrast medium is greatly different. The contrast medium has notable non-linearity and shows a response having a wide band with respect to the irradiated fundamental wave component $f_0$, but the organic tissue has only secondary effects in its non-linearity. Therefore, in the ultrasonic signal irradiated to the contrast medium, the spectrum of the response signal of the contrast medium is discriminated from the double higher harmonic wave $2f_0$ included in the response signal from the organic tissue by performing frequency modulation, with $f_0$ as a central frequency, and shifting the spectrum of the response signal of the contrast medium from frequencies near $2f_0$, so that the improvement of the definition of the contrast medium image can be expected. This shift effect is particularly notable if irradiation is performed twice, and addition and subtraction between the response signals is carried out (third feature of the present invention).

(4) The non-linearity shown by the contrast medium is generally determined by the frequency, the amplitude and the phase of the ultrasonic sound pressure waveform first irradiated to the contrast medium, but it is almost uninfluenced by the frequency, the amplitude and the phase of a subsequent waveform. Accordingly, if first and second irradiations with differing frequencies, amplitudes and phases are carried out in a double irradiation system and the effective differences between the two responses of each radiation time are detected, it is possible to extract the non-linearity proper to the contrast medium which in not present in the non-linearity of the organic tissue. Thus, the spectrum of the response signal of the contrast medium is discriminated from the double higher harmonic wave $2f_0$ included in the response signal from the organic tissue by further shifting the spectrum of the response signal of the contrast medium to a band lower than a frequency near $2f_0$, so that the improvement of the definition of the contrast medium image can be expected (fourth feature of the present invention).

(5) In contrast to the irradiation ultrasonic frequency $f_0$, the higher harmonic wave from the contrast medium exists, but almost no higher harmonic wave from the organic tissue exists in a frequency band of $2.2f_0$ or more. Accordingly, if the band of the band pass filter is set to $2.2f_0$ to $2.8f_0$, as in the first feature, only the response signal from the contrast medium is extracted. However, the contrast medium signal in this band has an effective signal strength only when the transmitted wave sound pressure is sufficiently high (fifth feature of the present invention).

The present invention solves the above-described problems by the employing the above-described features (1) to (5). These features of the present invention will now be explained in more detail.

(First Feature)

The ultrasonic enhanced-contrast method of the present invention is characterized in that it employs an ultrasonic probe for transmitting and receiving an ultrasonic wave travelling between the ultrasonic probe and an organism, a transmitting section for transmitting an ultrasonic signal in the ultrasonic probe, a receiving section for processing a response signal of the ultrasonic wave received by said ultrasonic probe, a filter for extracting a specific frequency component from the processed response signal, a frequency setting section for setting a pass frequency band of said filter on the basis of the frequency band of the response signal from the contrast medium injected in said organism, and a control section for controlling the operation of said filter in the set pass band.

When the fundamental frequency component of the transmitted ultrasonic signal supplied from the ultrasonic probe is set to $f_0$, the pass band width of the filter is set within a range of $0.8f_0$ to $2.5f_0$. Here, the fundamental frequency component $f_0$ is preferably set to a frequency near a free resonance frequency of the contrast medium, as determined by the average particle diameter of the contrast medium being used, and it is about 2 MHz in the case of a contrast medium of 2 μm particle diameter as widely used.

Namely, the response signal of the contrast medium is distributed in a wide frequency band, and the signal strength is also high over the wide frequency band. In consideration of these matters, the response signal over the wide frequency band $0.8f_0$ to $2.5f_0$ is extracted by the band pass filter, not limiting the band pass to $2f_0$ as in the conventional method. Thus, the response signal of the contrast medium alone can be emphasized relative the response signal of the organic tissue localized near $2f_0$. In particular, the double higher harmonic wave component $2f_0$ from the organic tissue can be neglected in the case of a relatively weak sound pressure (initial time phase) and can be also neglected with respect to the response signal from a relatively shallow part near the probe. Accordingly, the selection of such frequency bands is extremely effective. p There is a case in which the higher harmonic wave component $2f_0$ of the organic tissue cannot be neglected, as mentioned above, in the case of a high sound pressure (latter period time phase) and a response signal from a relatively deep part far from the probe. In this case, the higher harmonic wave component $2f_0$ of the tissue is preferably removed by setting the band width of the band pass filter to $0.8f_0$ to $1.8f_0$. Namely, in this case, the higher harmonic wave component $2f_0$, which is the only component emphasized in the conventional method, is removed or attenuated. In this case, the higher harmonic wave component caused by the contrast medium and distributed near $2f_0$ is also attenuated, but the response signal of the contrast medium distributed in a wide frequency band near $0.8f_0$ to $1.8f_0$ is extracted. Accordingly, the wide frequency band makes up for such attenuation. Therefore, the contrast medium signal is emphasized in comparison with the tissue signal, and contrast medium imaging of high definition can be performed.

As explained with reference to FIGS. 2A and 2B, the strength of the higher harmonic wave component $2f_0$ within the response signal from the organic tissue is changed according to depth. Therefore, the time of the response signal from various depths is calculated, and the pass band width of the filter is desirably switched in real time, as the depth of the signal changes, to $0.8f_0$ to $1.8f_0$, when the response signal is from a depth deeper than a set depth such that the higher harmonic wave component $2f_0$ is attenuated, and to $0.8f_0$ to $2.5f_0$, when the response signal is from a shallow depth. A band-pass filter (pass band $0.8f_0$ to $1.8f_0$) and a band removing filter (removing band $1.8f_0$ to $2.2f_0$) having $2f_0$ as a central frequency can be used as the filter for attenuating the higher harmonic wave component $2f_0$.

In the band selection of the above-described filter, the fundamental wave component $f_0$ from the contrast medium is also extracted. However, the fundamental wave component of the organic tissue response signal existing near $f_0$ also includes a component caused by the breathing of a human body and heart pulsation. Accordingly, there is a case in which an artifact is caused in the contrast medium image. In this case, it is suitable to further narrow and set the pass band width of the filter to $1.2f_0$ to $1.8f_0$. This is because the artifact superposed on the fundamental wave response $f_0$ component of the organic tissue deteriorates the definition of the contrast enhanced image, since a frequency near $f_0$ is included as the pass band width in the above-mentioned filter band.

Thus, in comparison with the conventional method, the SN ratio (strength ratio of the contrast medium response signal and the tissue response signal) of the enhanced-contrast image can be improved by discriminating the higher harmonic wave component $2f_0$ from the tissue and the response signal from the contrast medium.

(Second Feature)

As mentioned above, the first feature of the present invention is directed to the pass band width of the filter of the receiving section being greatly widened in comparison with the conventional method in accordance with the distribution of the response signal of the contrast medium over a wide frequency band, so as to emphasize and extract the response signal component of the contrast medium. To further promote the effect of the first feature, the frequency of the ultrasonic wave irradiated to the contrast medium is preferably set over a wide band, and the ultrasonic transmitting section is desirably constructed so as to supply an ultrasonic signal, having plural frequency components, to the ultrasonic probe. A waveform formed by connecting the unit waveforms of different frequencies can be used as such a waveform. In this case, the average of the frequency components of the unit waveforms is set to the frequency $f_0$, similar to that in the feature 1.

Namely, since the contrast medium has a free resonance frequency distributed in accordance with its particle diameter distribution, more contrast media are efficiently made to respond to the irradiated ultrasonic wave by distributing the frequency spectrum of the irradiated ultrasonic wave in a wide band, so that the response signal of the entire contrast medium is reinforced. As a result, in contrast to the response signal of the organic tissue which has $f_0$ and $2f_0$ as centers, the response signal of the contrast medium appears at a strong level over a wider range. Accordingly, the higher harmonic wave of the contrast medium and the higher harmonic wave of the tissue are more easily discriminated from each other even after passing through the band-pass filter.

(Third Feature)

In the above-described first and second features, the case of enhanced-contrast performed on the basis of the response signal produced from one irradiation by the ultrasonic beam has been considered. However, the first and second features of the present invention are not limited to an enhanced-contrast method using one irradiation, but can also be applied to an enhanced-contrast method of a so-called double irradiation system (or plural irradiation system), as provided in this feature. The plural-time irradiation system is effective when the movement of the contrast medium and extinction due to destruction are detected in real time and are drawn. When the movement and the destruction of the contrast medium are detected, response signals at two different times, before and after the movement, or before and after the destruction, are required. However, in the one-time irradiation system, the time interval at a different time is generally limited by one frame time interval (e.g., 10 to 20 milliseconds). Accordingly, no one-time irradiation system is suitable for an object having fast blood flow and in a case for instantly detecting the destruction of the contrast medium. In a plural-time irradiation system, the ultrasonic beam is irradiated plural times in the same direction at a very short time interval (repetiting transmitting period: e.g., 0.1 millisecond), and the response signal corresponding to each irradiation is compared. Thus, it is possible to detect whether the contrast medium is moved from the focus of one ultrasonic beam to another place within a predetermined time interval, or whether the contrast medium is destroyed by comparing these response signals.

More specifically, the transmitting section has a function of transmitting M ultrasonic beams (M is a natural number of $\geq 2$) at specific time intervals in the same direction, and the ultrasonic signal of each time is constructed by the connection of unit waveforms of different frequencies and is transmitted so as to be asymmetrical with respect to polarity inversion. In conformity with this construction, the receiving section is characterized in that it constructionally has a function of aligning phases of the response signals of the ultrasonic signals of the plural (M) times, and a function of attenuating the response signal of the organic tissue by adding or subtracting the phase-processed response signals. In this case, it is preferable to set the average frequencies $f_0$ of the frequency component of each unit waveform constituting the transmitting signal of each irradiation to be equal.

Since the frequency component of each unit waveform used in the transmitted waveform is different, frequency modulation can be said to be performed within the waveform. When addition or subtraction is performed on the two phase-processed response signals from such two transmissions, it is possible to attenuate the double higher harmonic wave component $2f_0$ of the response signal from the organic tissue without the band filter. This can be done because the non-linear response of the tissue and the contrast medium are greatly different from each other, and the contrast medium has notable non-linearity and shows a different frequency band response, even when the transmitted fundamental wave component $f_0$ is slightly modulated in frequency. The effective difference of the frequency spectra of the two irradiations demonstrates a shift to the low frequency side ($1.5f_0$) of the spectrum of the response signal from the contrast medium. Namely, the frequency spectrum of the response signal of the contrast medium obtained by the adding or subtracting processing is emphasized in a band near $1.2f_0$ to $1.8f_0$ and is attenuated near $2f_0$. Thus, if the $1.5f_0$ component is extracted, it can be discriminated from the double higher harmonic wave $2f_0$, including the response signal from the organic tissue. As previously mentioned, this is because the higher harmonic wave from the organic tissue localizes near $2f_0$ in spite of such frequency modulation bias. Such an effective difference using two irradiations, with only the polarity inverted and without performing frequency modulation as in the conventional method exhibits a peak at $2f_0$, without causing such a shift. Therefore, it is difficult to discriminate and efficiently extract the higher harmonic wave component included in the response signal of the contrast medium from the higher harmonic wave component included in the response signal of the organic tissue because of superposition on the higher harmonic wave component by the organic tissue response signal localized near $2f_0$.

In the construction of the above-described transmitting section, it is preferable that the transmitting section has a function of transmitting the ultrasonic beam plural (M, a natural number of $M \geq 2$) times at a specific time interval in the same direction, and N-waveforms respectively having frequencies f1, f2, ..., fn, ..., fN (N is a natural number of $N \geq 2$) are connected. The frequency distribution width $\Delta f$ of the frequencies f1 to fN is set within a range of $0.0f_0$ to $0.4f_0$, where the average frequency of the frequencies f1 to fN is set to $f_0$, and the ultrasonic signals are transmitted so as to be asymmetrical with respect to polarity inversion relative to each other. In accordance with this construction, the response signal component of the contrast medium can be further emphasized. The frequency distribution width $\Delta f$ is not particularly limited, but preferably ranges from $0.1f_0$ to $0.4f_0$, and it is practical with regard to circuit construction if it falls in a range of $0.2f_0$ to $0.3f_0$.

A half cycle, one cycle or more of a sine wave can be used in the unit waveform forming the above-described waveform of each irradiation. Conversely, the unit may be finely set to be ¼ cycle or ⅛ cycle, and finally a chirp waveform alternately increasing and decreasing in frequency may be also used.

The waveform transmitted each time is represented by a code f(A, θ) prescribing a frequency f, an amplitude A and a starting phase θ. A first waveform is preferably set by connecting the N-unit waveforms with frequencies f1(A1, θ1)<f2(A2, θ2)< ... <fn(An, θn)< ... <fN(AN, θN), and setting the amplitude to A1=A2= ... =An = ... =AN and the starting phase to θ1=θ2= ... =θn= ... =θN=180°. A second waveform is preferably set by connecting the N-unit waveforms with frequencies f1'(A1', θ1')>f2'(A2', θ2')> ... >fn'(An', θn')> ... >fN'(AN', θN'), and setting the amplitude to A1'=A2'= ... =An'= ... =AN' and the starting phase to θ1'=θ2'= ... =θn'= ... =θN'=0°. Namely, in the first waveform and the second waveform, the frequency series of one is increasing and the other is decreasing, the starting phases are set to be the same, and the amplitude may be set to be the same or it may be also different. In this case, the response signal of the organic tissue is attenuated by addition-processing the phase-processed response signal.

Further, the transmitted first and second waveforms are preferably prescribed by a code f(A, θ), prescribing a frequency f, an amplitude A and a starting phase θ. The first waveform is set by connecting the N-unit waveforms with frequencies set so as to satisfy the inequality f1(A1, θ1)<f2(A2, θ2)< ... <fn(An, θn)< ... <fN(AN, θN), and setting the amplitude to A1=A2= ... =An= ... =AN and the starting phase to θ1=θ2= ... =θn= ... =θN=180°. The second waveform is set by connecting the N-unit waveforms with frequencies set to be f1'(A1', θ1')>f2'(A2', θ2')> ... >fn'(An', θn')> ... >fN'(AN', θN'), setting the amplitude to A1'=A2'= ... =An'= ... =AN' and setting the starting phase to be θ1'=θ2'= ... =θn'= ... =θN'=0°. In this case, the response signal from the organic tissue is attenuated by addition of the phase-processed response signal.

Here, this case is characterized in that the first transmitting waveform is set to a waveform having a starting phase of 180°, which starts by lowering (negative polarity side) and the N unit waveforms continue from a low frequency f1(< ... <fN), and the second transmitting waveform is reversely set to a waveform having a staring phase of 0° and starts by rising (positive polarity side) and the N unit waveforms continue from a high frequency fN'(> ... >f1'). Namely, when the ultrasonic wave is transmitted to the contrast medium with an initially falling waveform, an air bubble of the contrast medium is started from the expanded state, so that the frequency distribution of the response signal is shifted lower than the average frequency $f_0$. In contrast to this, when the ultrasonic wave is irradiated to the contrast medium in an initially rising waveform, the deformation of the contrast medium is started from the contracted state, so that the frequency distribution of the response signal is shifted higher than the average frequency $f_0$. Accordingly, there is the particular effect that the frequency distribution of the response signal of the contrast medium can be more efficiently shifted to a frequency lower than the double higher harmonic wave $2f_0$ by setting the codes of the first and second waveforms as mentioned above, and adding and subtracting the receiving signals of the two irradiations, and it is discriminated from the double higher harmonic wave component $2f_0$, from the organic tissue localized near $2f_0$ so that the response signal component of the contrast medium can be further emphasized.

In the above case, the frequency distribution widths $\Delta f$ (=fN−N1) and $\Delta f'$(f1'−fN') of f1 to fN and f1' to fN' are respectively preferably changed over time within a range of $0.0f_0$ to $0.4f_0$ depending on the depth of an ultrasonic irradiation focus. This is because, since no higher harmonic wave component from the organic tissue is yet generated at a shallow depth, no shift of the effective spectrum onto the low frequency side is required, and it is sufficient to set $\Delta f=0$, and the spectrum shift is required at a deep depth as the higher harmonic wave component of the organic tissue is generated. For similar reasons, the frequency distribution widths $\Delta f$ and $\Delta f'$ of f1 to fN and f1' to fN' for a predetermined time after the injection of the contrast medium, e.g., two minutes for irradiating the normal ultrasonic sound pressure, are preferably set to $0.0f_0$ since the higher harmonic wave component from the organic tissue is very weak then. Further, the frequency distribution widths $\Delta f$ and $\Delta f'$ of f1 to fN and f1' to fN' after the passage of two minutes, at which time a high sound pressure for destroying the contrast medium is irradiated, are preferably within the range of $0.0f_0$ to $0.4f_0$, since the higher harmonic wave component from the organic tissue is increased.

In this third feature, the receiving section has a filter for extracting a specific frequency component from the attenuated response signal of the organic tissue. The pass band width of this filter is preferably set to $0.8f_0$ to $1.8f_0$ with the average frequency $f_0$ as a reference. In accordance with this construction, the higher harmonic wave $2f_0$ of the organic tissue, which is unable to be removed by the above adding and subtracting processing, is further removed, and the signal component of the contrast medium can be emphasized. Further, the pass band width of the filter is more preferably set to $1.2f_0$ to $1.8f_0$. This is because detection of an artifact due to breathing, pulsation, etc. appearing near the fundamental frequency $f_0$, as previously mentioned, can be restrained in accordance with this construction. Further, the pass band width of the filter can be changed over time in accordance with the depth of the response signal or the irradiated ultrasonic sound pressure. For example, the band pass width of the filter can be widened (e.g., $0.8f_0$ to $2.5f_0$), in the case of a shallow part, in depth or the initial time phase, and can be narrowed (e.g., $1.2f_0$ to $1.f_0$), in case a deep part is scanned or in the latter time phase.

(Fourth Feature)

The third feature is characterized in that the frequencies f1, f2, ..., fn, ..., fN of the respective unit waveforms forming the first waveform and the second waveform are gradually increased or decreased, and the response signal of the contrast medium included in the effective difference of the two signals is shifted to the low frequency side, and it is discriminated from the higher harmonic wave component from the organic tissue. In contrast to this, the fourth feature characterized in is that the shift of the response signal of the contrast medium to a lower frequency is further emphasized by setting the amplitude A of at least the first half wave of the first waveform and the second waveform to be greater than the amplitude of the subsequent unit waveform. The non-linearity shown by the contrast medium is generally determined by the frequency, the amplitude and the phase of the ultrasonic sound pressure waveform, first irradiated to the contrast medium, and it is hardly at all influenced by the frequency, the amplitude and the phase of the subsequent waveform. Accordingly, in the double irradiation system, if different frequencies, amplitudes and phases are set in the first and second irradiations and the effective difference between the responses is detected, it is possible to extract the non-linearity proper to the contrast medium and not the non-linearity of the organic tissue: the spectrum shift to the low frequency side.

The present inventors have discovered this fourth feature in simulation and experimentally. Its physical theory background is not necessarily clearly known, but it can be easily explained if the contrast medium is considered as a certain kind of resonance body. Namely, it is considered that among the sound pressure waveforms irradiating the contrast medium, the frequency, the phase and the amplitude of a starting unit waveform will determine the starting response of the contrast medium. However, the subsequent behavior of the contrast medium, whose response is once determined by the starting unit waveform, has a tendency to respond similarly to the response determined by the initial response, even when the frequency, the phase and the amplitude of the subsequent unit waveform are changed. It can be just considered that this is because, normally, a system once resonated at a certain frequency does not readily make a response to an input shifted from that resonance frequency, and this tendency is all the greater in the case of the contrast medium because of its non-linearity. The fourth feature of the present invention is characterized in that the shift of the frequency spectrum is further emphasized and the contrast medium and the organic tissue are effectively discriminated from each other by setting the amplitude A of the starting unit waveform to be greater than the amplitude of the subsequent unit waveforms, this occurring because of this initial waveform dependence of the contrast medium response, in other words, initial transient response dependence.

More specifically, the first waveform and the second waveform are set by a code $f(A, \theta)$, prescribing a frequency $f$, an amplitude $A$ and a starting phase $\theta$. The first waveform is formed by setting the frequencies of the N-unit waveforms to be $f1(A1, \theta1) < f2(A2, \theta2) < \ldots < fn(An, \theta n) < \ldots < fN(AN, \theta N)$, setting the amplitude to $A1 > A2 > \ldots > An > \ldots > AN$ and the starting phase to $\theta1 = \theta2 = \ldots = \theta n = \ldots = \theta N = 180°$. The second waveform is formed by setting the frequencies of the N-unit waveforms to be $f1'(A1', \theta1') > f2'(A2', \theta2') > \ldots > fn'(An', \theta n') > \ldots > fN'(AN', \theta N')$, and setting the amplitude to $A1' > A2' > \ldots > An' > \ldots > AN'$ and the starting phase to $\theta1' = \theta2' = \ldots = \theta n' = \ldots = \theta N' = 0°$.

In the above-described case, it is preferable to equally set the average amplitudes of the waveform A to be $(A1 + \ldots + AN)/N$ and A' to be $(A1' + \ldots + AN')/N$. As mentioned in the feature 3, in each of the amplitude distribution widths $\Delta A(=A1-AN)$ and $\Delta A'(=AN'-A1)$ of A1 to AN and A1' to AN', $\Delta A$ is preferably within a range of 0.0 A to 0.5 A, depending on the ultrasonic irradiation focus depth, independently of the frequency distribution widths $\Delta f$ and $\Delta f'$, or by coordinating with the frequency distribution widths. It is also suitable to particularly set $\Delta A$ from 0.0 A to 0.3 A. This is because, since no higher harmonic wave component from the organic tissue is generated at a shallow depth, the above spectrum shift is not required, and it is sufficient to set $\Delta A=0$, and the spectrum shift is required at a deep depth as the higher harmonic wave component of the organic tissue is grown. Accordingly, for example, $\Delta A=0.3$ A. For similar reasons, it is preferable to set $\Delta A=0$ in the initial time phase after the injection of the contrast medium, and to set $\Delta A=0.3$ A in the latter time phase.

In this example, A=A'. However, when A and A' are set to be different from each other, e.g., when A>A', the present invention can be applied particularly to the case of a contrast medium distributed to a deep depth (a depth of 7 to 10 centimeters when the signal is 2 MHz). In particular, at the deep tissue, the generated higher harmonic wave component of the tissue is attenuated by the damping effect of the tissue. In contrast to this, the fundamental wave component of the response of the contrast medium is only slightly attenuated. Accordingly, at this depth, a larger contrast medium response can be obtained by irradiation at a frequency that is set as low as possible. When A>A', the low frequency component of $f1(<f1')$ is emphasized since $(f1 + \ldots + fN)/N = (f1' + \ldots + fN')/N = f_0$. For example, when $f1=f2'=1.8$ MHz, $f2=f1'=2.2$ MHz and $f_0=2$ MHz and A=2*A', 1.8 MHz is emphasized by such amplitude weighting, and an increase in penetration of the contrast medium due to an effective low frequency shift of the irradiated ultrasonic wave reaches about 3 centimeters with 6 dB. At the shallow depth, such emphasis is naturally not required and A=A' is acceptable.

Summarizing the above, in feature 4 the values of the frequency distribution widths $\Delta f$ and $\Delta f'$, the amplitude distribution widths $\Delta A$ and $\Delta A'$ and the amplitude weight (A/A') are set independently or in coordination in the execution of the feature 4, as appropriate for the ultrasonic irradiation focus depth, or the time that has passed since the injection of the contrast medium.

(Fifth Feature)

With respect to the irradiated ultrasonic frequency $f_0$, a higher harmonic wave response signal in a frequency band of 2.2 f0 or more from the contrast medium is generated, but almost no such wave from the organism tissue is generated. Accordingly, if the band of the band-pass filter is set to $2.2f_0$ to $2.8f_0$ as in the first feature, only the response signal from the contrast medium is extracted. However, the contrast medium signal in this band has an effective signal strength only when the transmitted wave sound pressure is sufficiently high. If only the response from the contrast medium is considered, the high frequency limit is not limited to $2.8f_0$, but about $2.8f_0$ is a high frequency limit in view of the frequency characteristics of the ultrasonic probe for transmitting and receiving a signal. This fifth feature is efficient in the case of one-time irradiation, as in the features 1 and 2, but it can be also applied to a case in which the irradiation is performed twice and an effective difference is calculated, as will be described later.

In the above explanation, the transmitting waveform of the ultrasonic signal that is supplied to the ultrasonic probe has been described, but the present invention also dictates the waveform of the ultrasonic sound pressure applied to the contrast medium itself for the following reasons. In the frequency response characteristics of recent ultrasonic probes, the relative band is 60% or more with respect to a central frequency, and the (electric) transmitted waveform is very similar to the (acoustic) transmitted waveform. The effect formed with respect to the waveform of the ultrasonic signal supplied to the ultrasonic probe also holds true with respect to the acoustic waveform, i.e., the ultrasonic sound pressure waveform applied to the contrast medium. However, since it is necessary to transmit and receive the ultrasonic wave of a wider band in the fifth feature in comparison with the first to fourth features, the frequency response of the ultrasonic probe is preferably set to 75% or more of the central frequency. Further, a weight, such as a Hanning weight, etc., is desirably multiplied in the time axis direction in transmitted wave signals having a sine wave of one cycle as the unit waveform and connected unit waveforms with different amplitude and frequency. This is because, since the initial waveform dependence and the initial transient response dependence of the contrast medium are used in the features 3 and 4, the rapid rise and fall of the starting waveform cause an unnecessary response from the contrast medium.

BEST MODE FOR CARRYING OUT THE INVENTION

Figure 1:
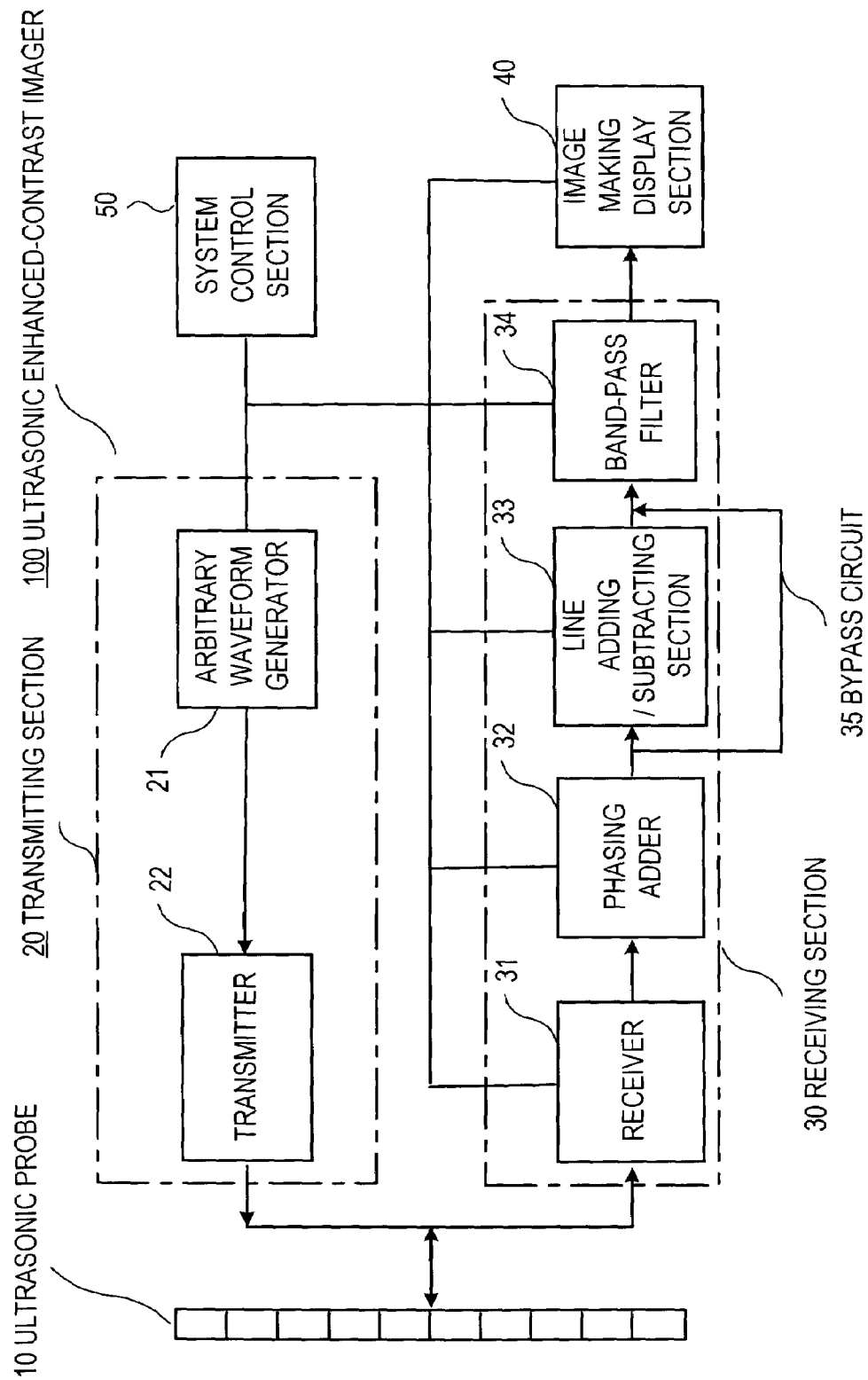
FIG. 1 is a block diagram showing the configuration of an ultrasonic enhanced-contrast imager according to a first embodiment of the present invention.

The present invention will be explained on the basis of the embodiments shown in the drawings; however, the present invention is not limited to these embodiments.

First Embodiment

FIG. 1 is a block diagram showing the overall configuration of an ultrasonic enhanced-contrast imager according to a first embodiment of the present invention. This embodiment is suitable for the execution of the afore-mentioned first and second features of the present invention. As shown in FIG. 1, an ultrasonic enhanced-contrast imager 100 comprises an ultrasonic probe 10, a transmitting section 20, a receiving section 30, an image making display section 40 and a system control section 50. The transmitting section 20 comprises an arbitrary waveform generator 21 and a transmitter 22. The receiving section 30 comprises a receiver 31, a phasing adder 32, a line adding/subtracting unit 33, a band-pass filter 34 and a bypass circuit 35.

Figure 2A:
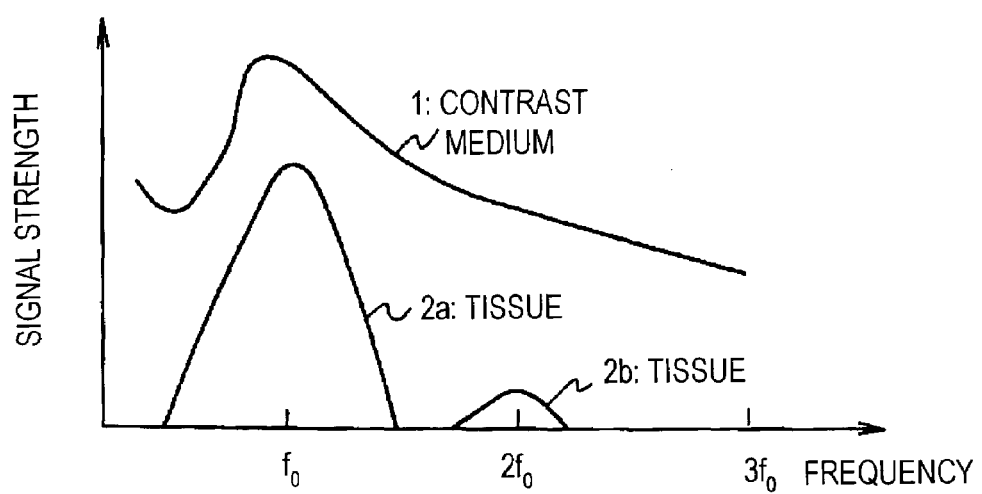
FIGS. 2A and 2B are graphs showing a model response spectrum of a contrast medium and of tissue, illustrating features of the present invention.
Figure 2B:
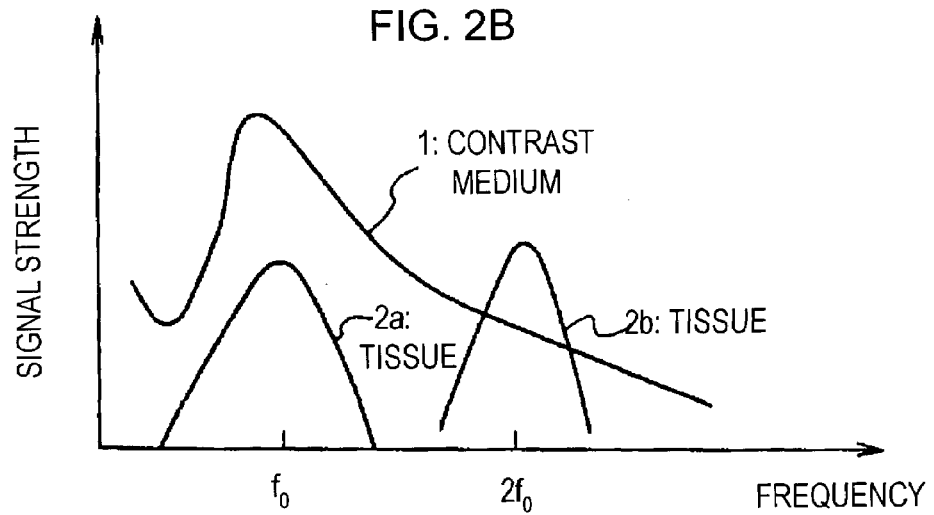

When the first feature is realized, the arbitrary waveform generator 21 of the transmitting section 20 is constructed so as to generate an ultrasonic pulse signal having a single frequency component $f_0$. When the second feature is realized, the arbitrary waveform generator 21 is constructed so as to generate an ultrasonic signal comprising unit waveforms having different frequency components f1, f2, and having $f_0$ as their average frequency, as in a waveform 51 shown in FIG. 3. The output of the arbitrary waveform generator 21 is supplied to the ultrasonic probe 10 of a wide band type through the transmitter 22. As shown in FIG. 1, the ultrasonic probe 10 is an array type probe, and is constructed to include several hundred element vibrators. Power amplifiers of a required number of channels corresponding to the number of elements of the array type ultrasonic probe 10 are arranged in parallel in an output section of the transmitter 22. Thus, the ultrasonic pulse of the average frequency $f_0$ is irradiated from the ultrasonic probe 10 to tissue. A response signal from a contrast medium distributed in the tissue and a response signal from the tissue itself are received by the ultrasonic probe 10 as a mixed ultrasonic signal. As shown in FIG. 2, the response signal from the contrast medium includes a higher harmonic wave component over a wide frequency band in addition to the component of the fundamental wave $f_0$. The response signal from the tissue includes the component of the fundamental wave $f_0$ and the component of a double higher harmonic wave $2f_0$.

The response signal received by the ultrasonic probe 10 is inputted to the receiver 31. The receiver 31 has a preamplifier of a required number of channels corresponding to the number of elements of the ultrasonic probe 10, a TGC amplifier, an A/D converter, etc. The receiver 31 amplifies and processes the inputted response signal and then it converts the processed signal to a digital signal, and outputs the digital signal to the phasing adder 32. The phasing adder 32 phases and adds a delay difference or a phase difference of the response signals from plural element vibrators relating to one ultrasonic beam. As is well known, the operation of such a phasing adder accomplishes scanning and focus of the ultrasonic beam, but the phasing adder is desirably a so-called digital beam former to minimize the generation of distortion during addition processing. This is so that no unnecessary higher harmonic wave $2f_0$ component is generated by the phasing addition processing.

The response signal phased and added by the phasing adder 32 is supplied to the band-pass filter 34. The band width of the band-pass filter 34 can be variably adjusted by the system control section 50, as will be described later. The adjustment of the band-pass width can be realized by using, as the band-pass filter 34, a digital filter, known as an FIR filter, and varying each coefficient series of this digital FIR filter in accordance with the depth or the ultrasonic sound pressure by the system control section 50. The digital filter preferably comprises a third order Chebyshev type filter. The response signal having a frequency component selected and extracted in the band-pass filter 34 is directly sent to the image making display section 40 in the realization of the first and second features. The image making display section 40 performs processing, including normal wave detection, image processing of a normal B-mode image, such as compression, Doppler processing, such as a color flow, or scanning conversion processing. The same processing as that of the normal B-mode image, such as wave detection, compression and scanning conversion is performed with respect to the contrast medium mode image.

The above-described processing operation is executed a number of times as required to cover a predetermined section or area of the organic tissue by scanning in the direction of the ultrasonic beam. The distribution and the size of the contrast medium is then displayed in a display monitor section (not shown) in the form of image information, such as brightness, by the processing of the image making display section 40. The system control section 50 controls this series of operations. The characteristic operation of the embodiment of FIG. 1, constructed in this way, will be explained. With respect to the picked-up image of the contrast medium mode executed by injecting the contrast medium, e.g., a B-mode fault image is picked up and displayed in the display monitor in advance. The contrast mode image obtained in the above-described operation is overlapped with this B-mode image and is displayed, or only the contrast medium mode image is independently displayed.

First, in the normal B-mode imaging, an ultrasonic signal having a single frequency in the form of the fundamental frequency $f_0$ is generated from the arbitrary waveform generator 21 on the basis of a control signal from the system control section 50, and wave focus processing is performed in the transmitter 22. Thereafter, the processed signal is amplified and supplied to the ultrasonic probe 10, and the ultrasonic beam is transmitted to the organism. A response signal from the organism is detected by the ultrasonic probe 10, amplified by the receiver 31 and converted to a digital signal. Thereafter, the phases (delay times) of the response signals from the same part received by plural vibrators are combined with each other in the phasing adder 32. With respect to every response signal phased and added, the response signal of a specific frequency component is selected and extracted by the band-pass filter 34. In the case of the picked-up image of the normal B-mode, the band of the band-pass filter 34 is adjusted to have the fundamental frequency $f_0$ as its central frequency. The image making display section 40 performs wave detection processing of the output of the band-pass filter 34, and it also performs image processing, such as compression or scanning conversion processing, a two-dimensional image (B-mode) of the tissue, and generates this image in the display section (display).

The scanning and the generation of the contrast medium mode image in accordance with the present invention will be explained. The basic procedure and operation of the scanning and the generation of the contrast medium mode image are similar to those of the normal B-mode picked-up image.

(Case Realizing the First Feature)

When the first feature of the present invention is realized by using the embodiment of FIG. 1, an ultrasonic signal having the single fundamental frequency $f_0$ is generated from the arbitrary waveform generator 21, and an ultrasonic beam (f1<$f_0$<f2 in FIG. 3) is transmitted to a predetermined part of the organism, as in scanning of tissue. As previously mentioned, in this ultrasonic signal, a Hanning weighting is applied in the time axis direction, and thus unnecessary response of the contrast medium is avoided. Further, with respect to the response signal from the organism, amplification and phasing processing are performed by the receiver 31 and the phasing adder 32, as in scanning of tissue.

The element relating to the first feature of the present invention is the band-pass filter 34 for extracting, from the phase-processed response signal, the component from the contrast medium. Namely, as explained with reference to FIG. 2, in comparison with the fundamental wave component 2a and the higher harmonic wave component 2b of the response signal from the tissue, the response signal 1 from the contrast medium has a high signal strength over a wide frequency band. Therefore, this embodiment is characterized in that the band pass width of the band-pass filter 34 is widened in comparison with the prior art, and the response signal from the contrast medium is emphasized with respect to the response signal from the tissue. In particular, it is desirable to variably adjust the band width of the band-pass filter 34 as in the following cases (A), (B) and (C).

(A) The band width of the band-pass filter 34 is set to be from $0.8f_0$ to $2.5f_0$ in the case where the contrast medium is in a shallow location. It is set to be from $0.8f_0$ to $1.8f_0$ in the case of a deep location, and it is preferably set to be from $1.2f_0$ to $1.8f_0$ (or $1.1f_0$ to $1.8f_0$).

(B) In the initial time phase after the injection of the contrast medium, the amplitude of the transmitted ultrasonic signal is set to a low sound pressure (mechanical index: MI=0.4 to about 0.7). Similar to the case of a shallow location, the band pass width is set to be from $0.8f_0$ to $1.8f_0$.

(C) In the latter time phase after the injection of the contrast medium, the amplitude of the transmitted ultrasonic signal is set to be a high sound pressure (mechanical index: MI=1.0 to about 1.3), and the band width of the band-pass filter 34 is changed to be from $0.8f_0$ to $1.8f_0$, and is preferably changed to be from $1.2f_0$ to $1.8f_0$ (or $1.1f_0$ to $1.8f_0$), in coordination with the amplitude.

This is because the higher harmonic wave component $2f_0$ of the tissue can be neglected in the case of a relatively weak sound pressure and the initial time phase. In this case, the response signal of the contrast medium can be emphasized over the response signal of the tissue by extracting the response signal over a wide frequency band of $0.8f_0$ to $2.5f_0$. In the case of a deep location, the higher harmonic wave component $2f_0$ from the tissue is strengthened, but the response signal of the contrast medium can be emphasized more than it could in the prior art, even when the response signal is extracted over the frequency band of $0.8f_0$ to $2.5f_0$. In contrast to this, when a high sound pressure is used as in the latter period time phase, the higher harmonic wave component $2f_0$ from the tissue cannot be neglected. Accordingly, the band width is set to $0.8f_0$ to $1.8f_0$ and the higher harmonic wave component $2f_0$ of the tissue is removed or attenuated. In this case, the high frequency component from the contrast medium near $2f_0$ is also attenuated, but the amount is slight because the whole response signal of the contrast medium is distributed over a wide frequency band. When the fundamental wave component of the response signal of the tissue existing near $f_0$ includes a component caused by breathing and pulsation of the human body and this causes an artifact in the contrast medium image, it is preferable to slightly narrow the pass band width of the filter to be from $1.2f_0$ to $1.8f_0$ (or $1.1f_0$ to $1.8f_0$).

Switching of such a band width is controlled by the system control section 50 based on the set transmitting wave focus or receiving wave focus. For example, since the depth of the response signal corresponds to the time axis of the response signal, the system control section 50 sets the band width to $0.8f_0$ to $2.5f_0$ in a range in which the time-related position of the response signal inputted to the band-pass filter 34 is shallower than a set depth, and the system control section 50 is switched to $1.2f_0$ to $1.8f_0$ when the focus is in a deep range in real time. For example, a deep location is 4 centimeters when the fundamental frequency $f_0$ is 2 MHz. Here, the two band widths are switched to correspond with two depth areas to make the explanation simple, but the band width also may be continuously narrowed in the depth direction.

The higher harmonic wave $2f_0$ of the tissue and the higher harmonic wave included in the response signal of the contrast medium can be discriminated by adjusting the band width of the band-pass filter 34 in this way. The SN ratio (strength ratio of the contrast medium response signal and the tissue response signal) of an enhanced-contrast image can be improved in comparison with the prior art by detecting and extracting the higher harmonic wave component of the response signal from the contrast medium in order to detect and image it. The filter for attenuating the higher harmonic wave component $2f_0$ may be constructed by using the band-pass filter 34, and it also may be constructed by using a band removing filter having a central frequency of $2f_0$ by changing the coefficient series of the digital FIR filter constituting the band-pass filter.

(Case Realizing the Second Feature)

Figure 3:
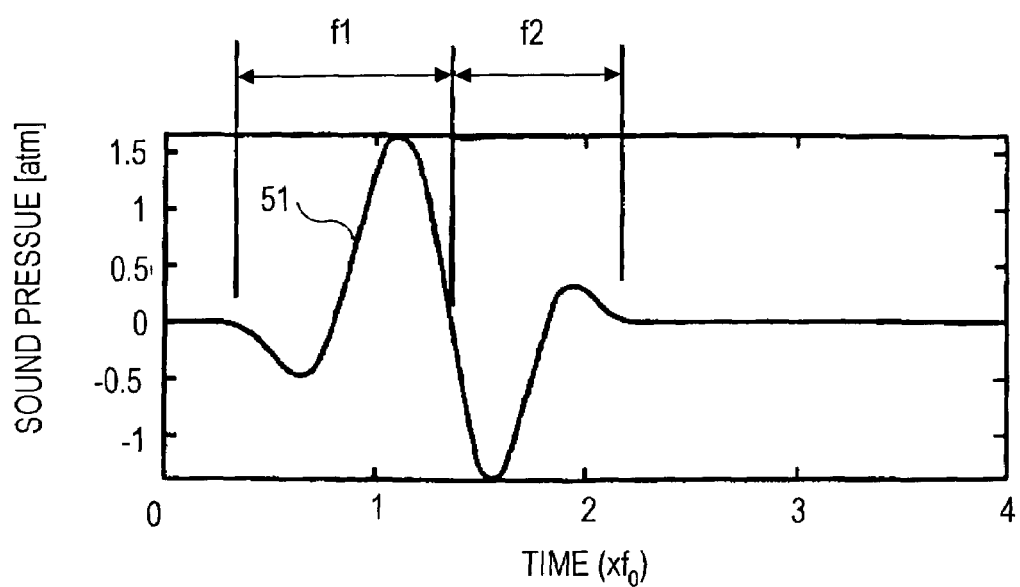
FIG. 3 is a graph showing one example of the transmission waveform of an ultrasonic wave in accordance with the first embodiment of the present invention.

As mentioned above, in the first feature, the pass band width of the band-pass filter 34 is widened and varied in accordance with depth of scanning, the time phase and the sound pressure so that extraction of the component of response signal from the contrast medium is emphasized over the response signal from the tissue. To further promote this effect, the second feature of the present invention is characterized in that the frequency spectrum of the ultrasonic wave transmitted to the contrast medium is made wide in comparison with the conventional case. For example, the ultrasonic signal generated by the arbitrary waveform generator 21 is set to have frequency component units with different respective waveforms, so that plural frequency components make up the entire waveform, with $f_0$ as an average of the respective frequency components, as in the waveform 51 shown in FIG. 3. Thus, a signal having frequency components of a range wider than that of the first feature is set. In FIG. 3, the waveform 51 has unit waveforms in which one sine wave cycle of frequencies f1, f2 is continued. The average frequency of these frequencies f1, f2 is $f_0$ ($f_0=(f1+f2)/2$). In the illustrated example, f1<f2. With respect to the average frequency $f_0$, a frequency suitable for the tissue and the device, matching the response band of the ultrasonic probe, is selected. Further, Hanning weighting is applied in the time axis direction, and thus an unnecessary response from the contrast medium is avoided. The effects of the present invention are the same even with an ultrasonic signal having a waveform obtained by inverting the polarity of the waveform 51 (rising at the start), and a waveform inverted (f1>f2) with respect to the time axis. The response signal of the contrast medium is strengthened over a wide frequency spectrum by transmitting an ultrasonic signal, which is constructed by the connection of unit waveforms having such plural frequency components, to the organism. Since the contrast medium has a free resonance frequency distribution corresponding to its particle diameter distribution, more contrast media produce a response, and the response signal of the contrast medium itself is reinforced by widening the frequency spectrum of the transmitted ultrasonic wave.

In accordance with the second feature, $f_0$ and $2f_0$ are set to be centers of the response signal from the tissue as previously mentioned. However, since the response signal of the contrast medium is at a strong level over a wider frequency band, the higher harmonic wave of the tissue and the higher harmonic wave of the contrast medium are more easily discriminated from each other. Here, the absolute value |f1−f2| of the difference of frequencies f1, f2, i.e., the distribution width $\Delta f$ of the waveform unit frequencies, is selected within a range of $0.0f_0$ to $0.4f_0$. The distribution width $\Delta f$ is preferably set to $0.1f_0$ to $0.4f_0$, and it is more preferably set to $0.2f_0$ to $0.3f_0$. The output of the arbitrary waveform generator 21 is not limited to a unit waveform series having the above two frequencies f1, f2, but a waveform having N(N≧2) frequencies can be used, as will be described later.

Second Embodiment

The overall configuration of an ultrasonic enhanced-contrast imager according to an embodiment suitable for the realization of the third and fourth features of the present invention is also shown in FIG. 1. In this figure, this embodiment differs from the first embodiment in that a line adding/subtracting device 33 is newly arranged between the phasing adder 32 and the band-pass filter 34. Namely, the ultrasonic signal is transmitted twice at a specific time interval in the same direction as the ultrasonic beam, and an image emphasizing the response signal of the contrast medium is obtained by adding and subtracting the response signals of the first and second ultrasonic signals.

Figure 4A:
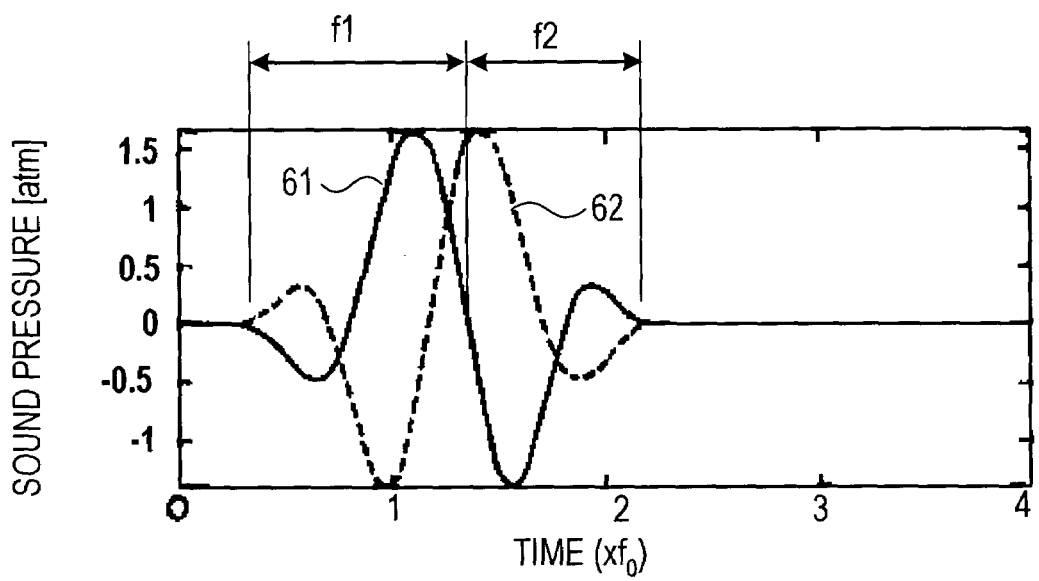
FIGS. 4A and 4B are graphs showing one example of the ultrasonic transmission waveform of two irradiations relating to frequency emphasis of the first embodiment of the present invention, and the simulation result of frequency spectra of a transmission signal and a response signal obtained by this transmission waveform.

In the third feature of the present invention in this embodiment, the arbitrary waveform generator 21 is constructed so as to generate an ultrasonic signal having a first waveform 61 (or 62), as shown in FIG. 4A. The first waveform 61 has the same requirements as the waveform shown in FIG. 3. The second waveform 62 is one in which the frequencies f1 f2 of the unit waveforms in the first waveform 61 are assigned in the reverse order. However, the second waveform 62 is asymmetric with respect to polarity inversion, as in the prior art. As will be described later, the first waveform 61 and the second waveform 62 can be coded for frequency, starting phase and amplitude, and an arbitrary waveform can be generated by connecting the coded one-cycle waveforms.

The arbitrary waveform generator 21 alternately generates the ultrasonic signals of the first waveform 61 and the second waveform 62 of FIG. 4A, as controlled by the system control section 50, at a predetermined time interval in the same ultrasonic beam direction. Each waveform is inputted to the ultrasonic probe 10 through the transmitter 22. Such waveforms can be easily produced by having the system control section 50 supply digital data, obtained by sampling analog signals of the above first waveform 61 and the second waveform 62, to a D/A converter. Further, selection of the frequency f1 or f2, the control of the number of unit waveforms to be connected, and amplitude modulation such as the Hanning weight, etc., are calculated in advance, and these values are stored in a memory device, such as a memory within the system control section (not shown), and are selected and executed by a program for every transmission by a computer (not shown) in the system control section 50.

When the ultrasonic signals of the first waveform 61 and the second waveform 62 are transmitted to the organism, two response signals to these ultrasonic signals are inputted to the receiver 31. These two response signals are responses to two ultrasonic beams in the same direction, and their times of input are separated from each other by a predetermined time interval. The response signals are amplified, A/D-converted and phase information is added in the receiver 31 and the phasing adder 32, and they are outputted to the line adding/subtracting device 33, each of these response signals having phase information added to it. The line adding/subtracting device 33 carries out RF adding and subtracting calculations, taking into account the phases of the two response signals, and calculates from the two response signals one response signal (RF line signal) to be displayed.

Thus, with respect to the response signal obtained by adding and subtracting the response signals of the two ultrasonic signal irradiations, the same component (linear component) included in the two response signals is attenuated, and a nonlinear component, such as a higher harmonic wave component of the contrast medium, the tissue, etc., is emphasized and inputted to the band-pass filter 34 in the third (or fourth) feature. The band-pass filter 34 has a construction similar to that explained in connection with the first embodiment, the pass band width varying in accordance with the depth of the response signal source and the time phase of the contrast medium as instructed by the system control section 50, and the response signal from a specific portion of the contrast medium is emphasized. The system control section 50 controls a series of operations relating to the arbitrary waveform generator 21, the receiver 31, the phasing adder 32, the line adding/subtracting device 33 and the band-pass filter 34.

Figure 4B:
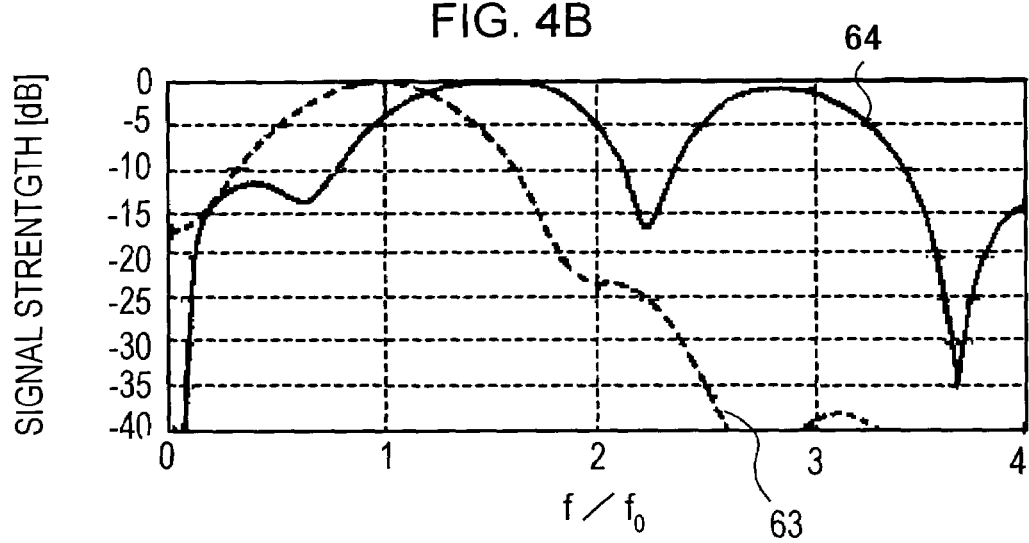

Here, the result of a simulation effectively emphasizing the response signal of the contrast medium using the first waveform 61 and the second waveform 62 to carry out contrast medium mode imaging, as shown in the FIG. 4A, will be explained. FIG. 4B shows a frequency spectrum obtained by simulating signals outputted from the line adding/subtracting device 33 when the ultrasonic signal of the first waveform 61 of FIG. 4A is first transmitted and the ultrasonic signal of the second waveform 62 of this figure is transmitted second. The axis of abscissa of FIG. 4B shows a frequency normalized at the fundamental frequency $f_0$, and the axis of ordinate shows signal strength normalized at the spectrum peak of a transmitting pulse. The broken line 63 in FIG. 4B shows the frequency spectrum of a transmitting ultrasonic wave, and the solid line 64 shows the frequency spectrum of the response signal outputted from the line adding/subtracting device 33.

In this simulation, in the first waveform 61 of the first transmission, the frequency is f1 (=1.8 MHz) in a first cycle, and it is f2 (=2.2 MHz) in the next cycle. The average frequency $f_0$ of the frequencies is set to be 2 MHz. In the second waveform 62 of the second transmission, the frequency is f2 (=2.2 MHz) in a first cycle, and it is f1(=1.8 MHz) in the next cycle. The average frequency $f_0$ of the frequencies is set to be 2 MHz. The coded "frequency f (amplitude A, starting phase θ)" previously mentioned for the first waveform 61 of the first transmission is 1.8 MHz (1.0, 180°) and 2.2 MHz (1.0, 180°). The code of the second waveform 62 of the second transmission is 2.2 MHz (1.0, 0°), and 1.8 MHz (1.0, 0°). Further, each of frequency variation ranges Δf, Δf' is 0.4 MHz, and the amplitude variation range AA is 0.0. In each waveform, Hanning weighting is further superposed in the time axis direction.

Further, in this simulation, the change in particle diameter of the contrast medium is calculated by a well-known differential equation, and this change of the contrast medium, when the sound pressure waveform of a mechanical index: MI=0.7 is irradiated to the contrast medium of 2 microns in diameter is calculated. An observation is made at an observing point distant from the contrast medium when vibration caused by this diametrical change is emitted as a secondary sound source. A simple air bubble within water is adopted as the contrast medium.

Figure 7:
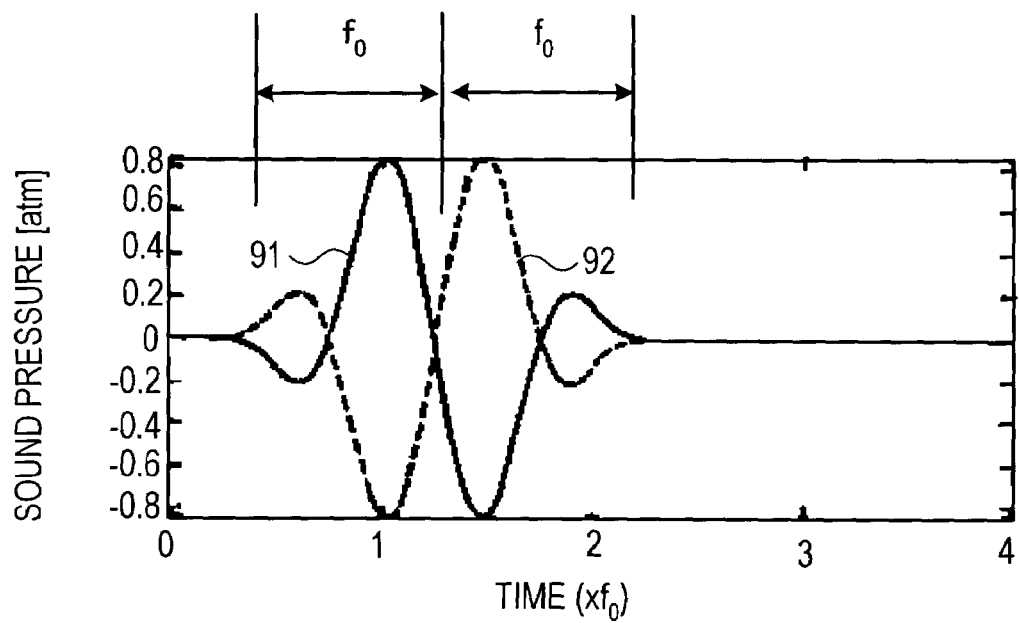
FIGS. 7A and 7B are graphs showing one example of the transmission waveform of two irradiations as used in the prior art, and the simulation result of frequency spectra of its transmission signal and an obtained response signal to compare the prior art and the present invention.
Figure 7B:
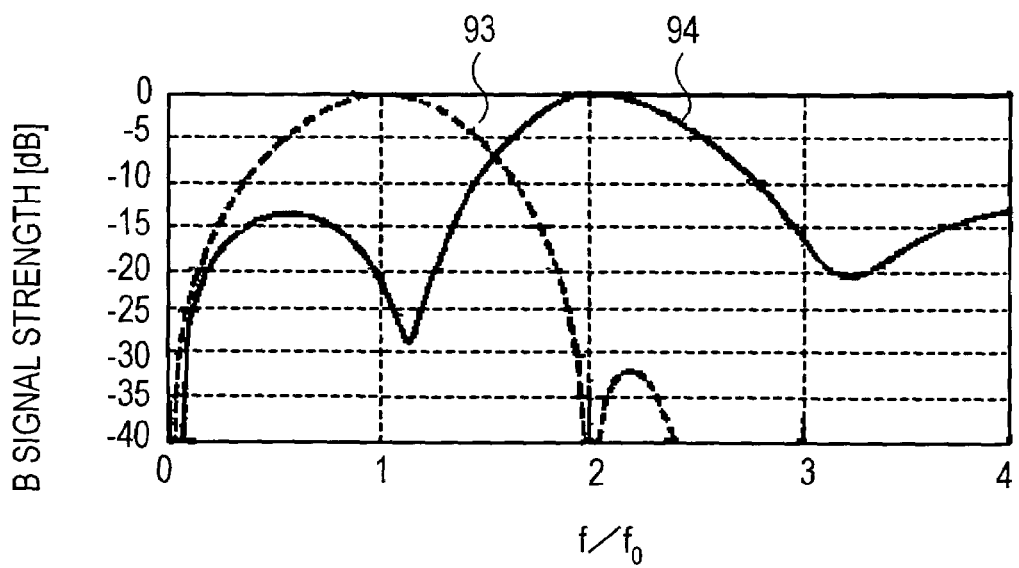

Here, the feature of the frequency spectrum of the response signal obtained by this embodiment, as shown in FIG. 4B, will be explained in comparison with the frequency spectrum of a double irradiation in the prior art. FIG. 7A shows an ultrasonic transmission waveform of the conventional system, and FIG. 7B shows frequency spectra of the transmission signal and the response signal. The axes of ordinate and abscissa of these FIGS. 7A and 7B are the same as the case of FIGS. 4A and 4B. In FIG. 7A, a first waveform 91 is that of the first transmission, and a second waveform 92 is that of the second transmission. Each of these frequencies is set to be the fundamental frequency $f_0$=2 MHz.

When the spectra of the solid line 64 of FIG. 4B and a solid line 94 of FIG. 7B are compared with each other, it is seen that the response signal near the fundamental frequency $f_0$ is greatly attenuated in the prior art, and the higher harmonic wave component of the tissue near $2f_0$ is emphasized. This is suitable for so-called tissue higher harmonic wave image picking-up (called Tissue Harmonic Imaging), but the response signal component of the contrast medium, which is widely distributed from $f_0$ to $2f_0$, is reversely attenuated. In particular, the fundamental frequency $f_0$, which is a main response signal of the contrast medium is greatly attenuated. Accordingly, in the case of the conventional double irradiating system shown in FIGS. 7A and 7B, it is impossible to satisfy the requirement that the response signal of the contrast medium is discriminated from the higher harmonic wave of the tissue and is emphasized and displayed. This is because the higher harmonic wave component of the tissue response signal locally existing near $2f_0$ is also emphasized, and the fundamental frequency $f_0$ component of the contrast medium response signal, which is distributed over a wide range, is greatly attenuated when the polarities or the time axes of the ultrasonic signal of the two transmissions in the prior art are mutually inverted.

On the other hand, in accordance with FIG. 4B, which illustrates the present invention, the output of the line adding/subtracting device 33 has a peak of the spectrum near $1.5f_0$, and it is attenuated near $2f_0$ at which the double higher harmonic wave component from the tissue localizes. Accordingly, it can be seen that the spectrum of the response signal from the contrast medium is shifted toward low frequencies in general. In the frequency modulation of an irradiation sound pressure waveform according to the third feature of the present invention, the spectrum of the response signal from the contrast medium is shifted toward the low frequencies, away from the double higher harmonic wave component included in the response signal from the organic tissue, which is an obstacle to imaging of the contrast medium, so that only the contrast medium-generated signal can be emphasized and extracted by the control of various kinds of band-pass filters, to be described later.

If the discrimination ratio of the contrast medium response signal and the higher harmonic wave of the tissue response signal is taken to be the energy ratio (area ratio) of the spectrum in the band ranging from $1.2f_0$ to $1.8f_0$ and the spectrum in the band ranging from $1.8f_0$ to $2.2f_0$, an improvement of approximately 10 dB to 20 dB is achieved in comparison with the prior art (FIGS. 7A and 7B).

The pass band width of the band-pass filter 34 is the same as that described relation to the second feature. Namely, a signal obtained by the line adding/subtracting device 32 includes the response signal from the contrast medium over a wide band from $0.8f_0$ to $2.5f_0$ in the imaging of a shallow location. Accordingly, this obtained signal can be taken to be a signal from the contrast medium and is imaged as it is. The same pass band is also set in the normal contrast medium in which the sound pressure of the ultrasonic wave is relatively low (e.g., mechanical index: MI value=0.2 to 0.7). In contrast to this, when the sound pressure of the ultrasonic wave is high (e.g., mechanical index: MI value=1.3), it is set to be from $0.8f_0$ to $1.8f_0$. The effect of the change in the band in this case is the attenuation of the frequency component near $2f_0$. Accordingly, this attenuation can be executed instead by the addition of a band removing filter with $2f_0$ as a central frequency, or by the removing filter itself. In the case of a deep location, it is preferable to change the band width to $1.2f_0$ to $1.8f_0$, so as to attenuate the higher harmonic wave caused by the tissue near $2f_0$, and to reduce an artifact at the fundamental wave caused by body movement. Thus, the response signal of the contrast medium can be emphasized more in the imaging in comparison with the second feature of the first embodiment.

Similar effects are also obtained when the frequencies f1, f2 of the first waveform 61 and the second waveform 62 of FIG. 4A are interchanged, i.e., when the relation of the frequency f1 of the first code and the frequency f2 of the second code is set to f1>f (not shown).

As mentioned above, in the second embodiment, each waveform of one cycle making up the transmission waveform of the ultrasonic wave is coded by the frequency f, the amplitude A and the starting phase 0, and their waveforms are connected. In particular, the second embodiment is characterized in that the frequency distribution of the transmitting signal of the ultrasonic wave that has been twice irradiated is biased by setting the frequencies of the first cycle of the first waveform 61 and the second waveform 62 to be different, as in the waveform shown in FIG. 4A. When the transmitting signal that has been emphasized in frequency in this way is transmitted twice and its response signals are added and processed, a shift of the frequency spectrum from a distribution (FIG. 7B: prior art) having a strong signal in a band with $2f_0$ as a center to a distribution (FIG. 4B: the present invention) having a strong signal from $1.2f_0$ to $1.8f_0$ is caused as is appropriate for the spectrum of the response signal from the contrast medium. The spectrum of the response signal of the contrast medium is not overlapped with the higher harmonic wave component $2f_0$ from the tissue because of this low frequency shift so that the response signal from the contrast medium can be emphasized and extracted by the above band-pass filter. It should be particularly emphasized here that this is greatly different from the prior art emphasizing $2f_0$.

The fourth feature of the present invention in the second embodiment can be realized by using the ultrasonic enhanced-contrast imager shown in FIG. 1. This embodiment differs from the above-described third feature in that the arbitrary waveform generator 21 is constructed so as to generate an ultrasonic signal in the first waveform 71 and the second waveform 72 shown in FIG. 5A and the first waveform 81 and the second waveform 82 shown in FIG. 6A. The other parts are similar to those in the ultrasonic enhanced-contrast imager shown in FIG. 1. Accordingly, the different points will be explained chiefly.

Figure 5A:
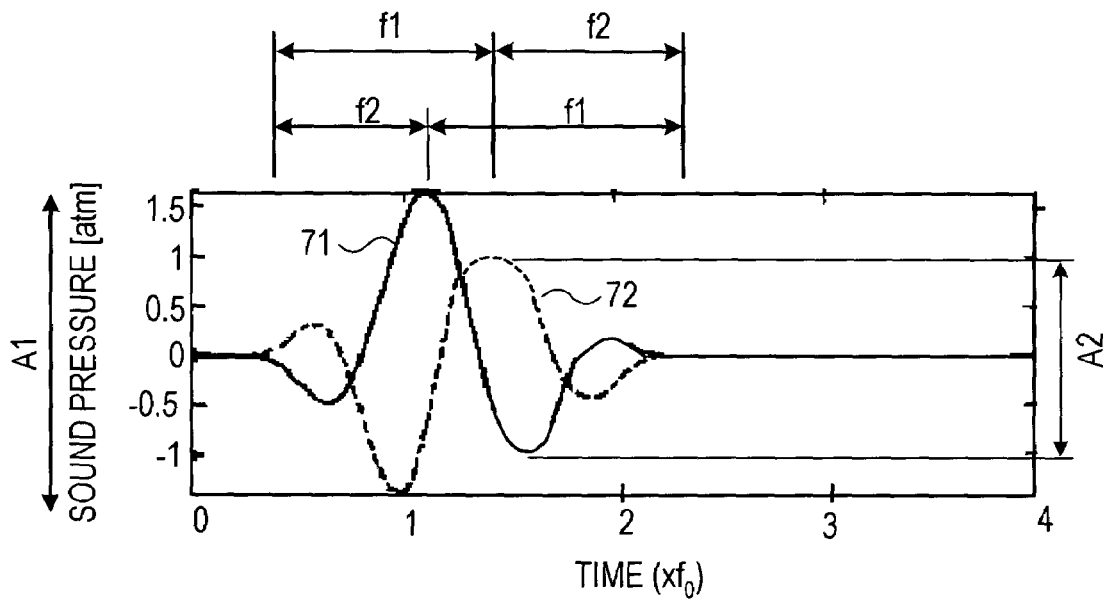
FIGS. 5A and 5B are graphs showing one example of the ultrasonic transmission waveform of two irradiations relating to frequency and amplitude emphasis of a second embodiment of the present invention, and the simulation result of frequency spectra of a transmission signal and a response signal obtained by this transmission waveform.
Figure 5B:
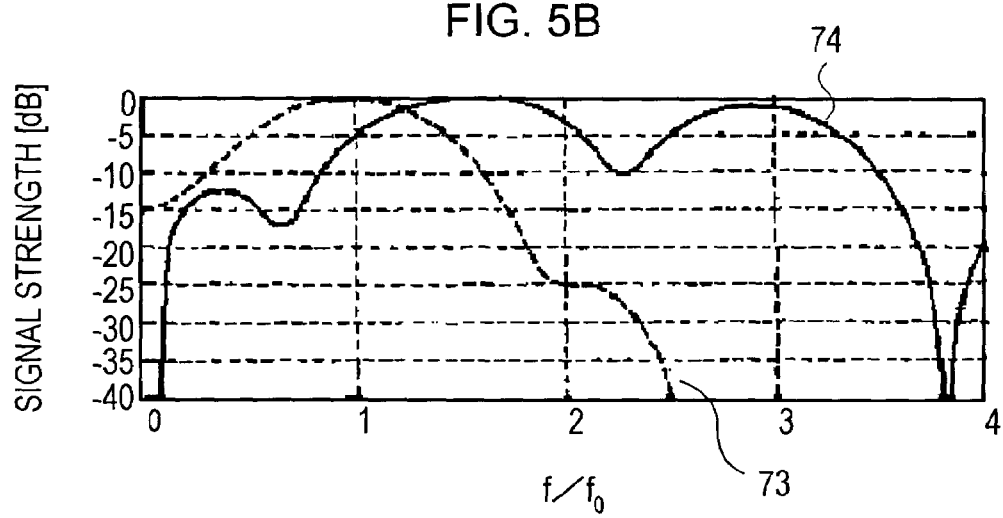
Figure 6A:
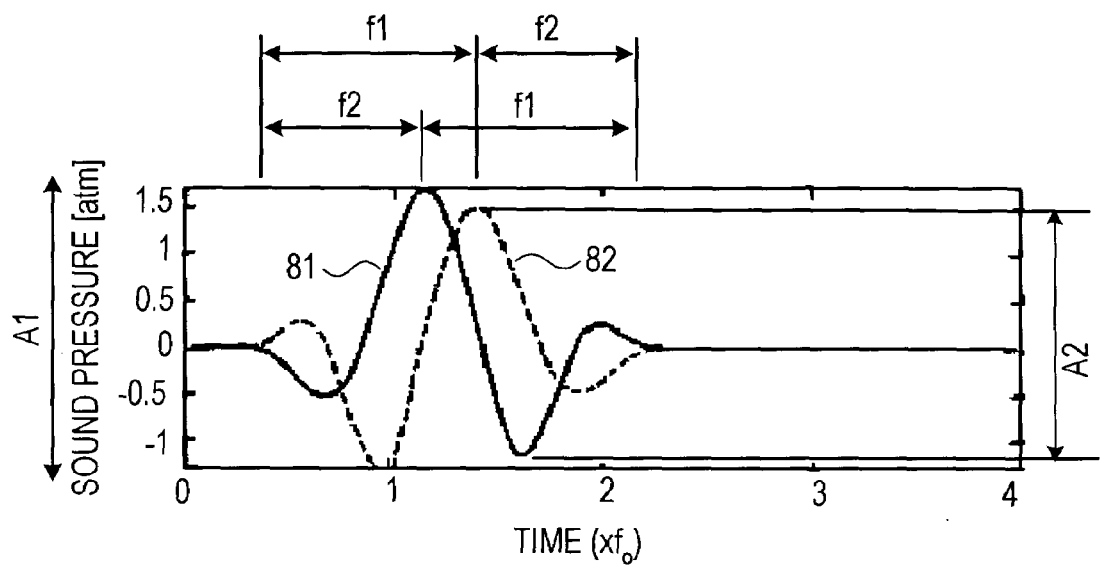
FIGS. 6A and 6B are graphs showing another example of the ultrasonic transmission waveform of the two irradiations relating to the frequency and the amplitude emphasis of the second embodiment of the present invention, and the simulation result of frequency spectra of the transmission signal and the response signal obtained by this transmission waveform.
Figure 6B:
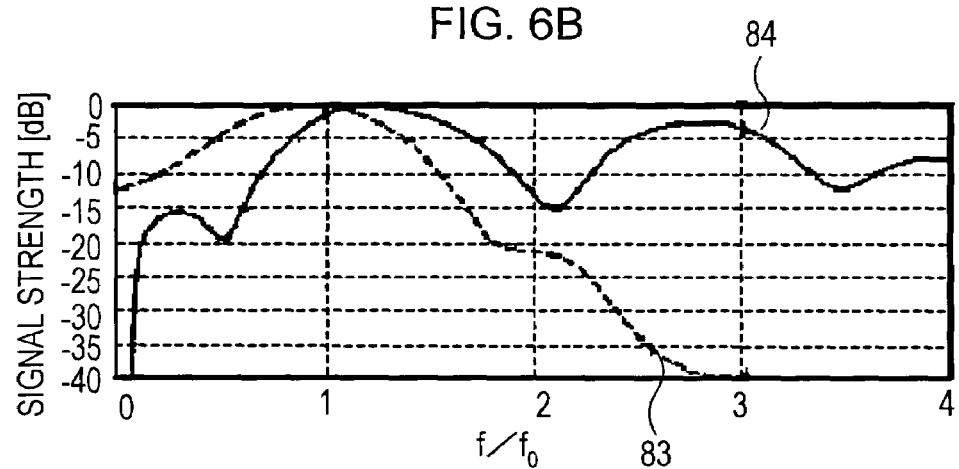

FIGS. 5A and 6A differ from FIG. 4A in that the amplitudes of the unit waveform of the first cycle of the first waveform and the second waveform are set to be greater than the amplitude of subsequent unit waveforms. FIGS. 5B and 6B show simulation results similar to those of FIG. 4B. Broken lines 73, 83 show frequency spectra of the transmitted ultrasonic wave, and solid lines 74, 84 show frequency spectra of the response signal of the contrast medium with lines added and subtracted.

The codes f (A, 0) of the first waveform 71 of FIG. 5A are, in order, 1.7 MHz (1.1, 180°) and 2.3 MHz (0.8, 0°), and the codes f (A, theta) of the second waveform 72 are, in order, 2.3 MHz (1.1, 0°) and 1.7 MHz (0.8, 180°). Their average frequency is 2 MHz. In other words, the frequency changing width Δf is set to 0.6 MHz, as opposed to 0.4 MHz of FIG. 4, and the amplitude changing width AA is set to 0.3, as opposed to 0.0 of FIG. 4.

With the ultrasonic waveforms of FIG. 5A, the spectrum of the response signal from the contrast medium obtained by adding the response signals corresponding to the two ultrasonic transmissions is shifted toward the fundamental wave $f_0$, and it has a peak near $1.5f_0$, as can be seen from FIG. 5B in this case. In comparison with FIG. 4B, the attenuating effect with respect to the higher harmonic wave component $2f_0$ included in the response signal from the tissue is slightly inferior, but the distribution of the response signal from the contrast medium obtained by the addition can be emphasized over the higher harmonic wave from the tissue by extraction with the band-pass filter set to $1.2f_0$ to $1.8f_0$. Further, as described in the third feature, when no movements of the tissue and the contrast medium caused by breathing and pulsation are notable, the band-pass filter is further widened ($0.8f_0$ to $1.8f_0$) in frequency and the energy ratio of higher harmonic waves from the contrast medium with the higher harmonic wave from tissue is high so that the discrimination ratio can be improved.

The codes f (A, 0) of the first waveform 81 of FIG. 6A are, in order, 1.8 MHz (1.0, 180°) and 2.2 MHz (0.9, 0°), and the codes f (A, 0) of the second waveform 82 are, in order, 2.2 MHz (1.0, 0°) and 1.8 MHz (0.9, 180°). Their average frequency is 2 MHz. Namely, the frequency variation range Δf is 0.4 MHz, the same as FIG. 4A, and the amplitude variation range AA is set to be 0.1 in contrast to 0.0 of FIG. 4A.

As a result, with the ultrasonic waveforms of FIG. 6A, the spectrum of the response signal from the contrast medium obtained by adding the response signals corresponding to the two ultrasonic transmissions is also shifted toward the fundamental wave $f_0$, and it has a peak near $1.5f_0$, as can be seen from FIG. 6B in this case. In this case, the attenuating effect with respect to the higher harmonic wave component $2f_0$ included in the response signal from the tissue is 15 dB, in comparison with about 5 dB of FIG. 4B and is therefore improved. Further, the frequency component corresponding to the triple-frequency harmonic wave in the response of the contrast medium is shifted to $2.5f_0$, so that it is suitable for a case in which the fifth feature for extracting a frequency band almost having no higher harmonic wave from the tissue is executed. In FIG. 7B, representing the prior art, and in FIGS. 4B and 5B, the corresponding spectrum peak is near $3f_0$, and it should be emphasized that this peak lies outside the frequency response range in the ultrasonic probe having a normal ratio band, as mentioned above.

In the above-described embodiment, the case of the double irradiation of the ultrasonic wave with a time interval between the two will be considered. In accordance with the present invention, no simulation result is shown with respect to a case in which the ultrasonic wave is irradiated three times or more. However, for example, the device is formed so that the codes f (A, 0) of the first waveform are, in order, 1.8 MHz (1.1, 180°) and 2.2 MHz (0.9, 0°), and the codes f (A, 0) of the second waveform are, in order, 2.0 MHz (1.1, 0°) and 2.0 MHz (1.0, 180°), and the codes f (A, 0) of a third waveform are, in order, 2.2 MHz (1.1, 180°) and 1.8 MHz (1.0, 0°). Their average frequency is set to 2 MHz.

In the explanation of the third and fourth features, the ultrasonic beam is irradiated in the same direction in the two signal transmissions. However, when the contrast medium is trapped to the tissue, as in the latter period time phase, the movement of the contrast medium is slight. Accordingly, no effects of the present invention are changed even when the directions of the two ultrasonic beams are slightly different.

The invention claimed is:

1. An ultrasonic enhanced-contrast imager for enabling enhancement of an image when utilizing a contrast medium, characterized in that it comprises an ultrasonic probe for transmitting an ultrasonic wave to an organism and for receiving an ultrasonic wave from the organism, a transmitting section for transmitting an ultrasonic signal to the ultrasonic probe, a receiving section for processing a response signal ultrasonic wave received by said ultrasonic probe, a filter for extracting a specific frequency component from the processed response signal, a setting control section for setting a width of the pass frequency band of said filter so as to enable discrimination of a response signal from a contrast medium injected to the organism with respect to a response signal from a tissue of the organism, and a control section for controlling the operation of said filter in the set pass band, wherein said setting control section sets the pass band of said filter to be in a range from $0.8f_0$ to $2.5f_0$, where $f_0$ is the average frequency of said ultrasonic signal transmitted to said ultrasonic probe.

2. The ultrasonic enhanced-contrast imager according to claim 1, wherein said setting control section sets the pass band width of said filter to be in the range from $0.8f_0$ to $1.8f_0$.

3. The ultrasonic enhanced-contrast imager according to claim 1, wherein said setting control section sets the pass band width of said filter to be in the range from $1.2f_0$ to $1.8f_0$.

4. The ultrasonic enhanced-contrast imager according to claim 1, wherein said transmitting section transmits said ultrasonic signal having plural frequency components to said ultrasonic probe.

5. The ultrasonic enhanced-contrast imager according to claim 4, wherein said ultrasonic signal has a continuous waveform formed by connecting the waveforms of different frequencies.

6. An ultrasonic enhanced-contrast imager according to claim 1, wherein the pass band of said filter is changed over time in accordance with a depth of the response signal.

7. An ultrasonic enhanced-contrast imager according to claim 6, wherein the pass band of said filter includes a second harmonic frequency for a shallow region and excludes a second harmonic frequency for a deep region.

8. An ultrasonic enhanced-contrast imager according to claim 1, wherein the pass band of the filter is changed over time in accordance with the time that has passed since the injection of the contrast medium.

9. An ultrasonic enhanced-contrast imager according to claim 8, wherein the pass band of the filter includes a second harmonic frequency for an initial time phase after the injection and excludes the second harmonic frequency for a later time phase after the injection.

10. The ultrasonic enhanced-contrast imager for enabling enhancement of an image when utilizing a contrast medium, characterized in that it comprises an ultrasonic probe for transmitting an ultrasonic wave to an organism and for receiving an ultrasonic wave from the organism, a transmitting section for transmitting an ultrasonic signal to the ultrasonic probe, a receiving section for processing a response signal ultrasonic wave received by said ultrasonic probe, a filter for extracting a specific frequency component from the processed response signal, a setting control section for setting the pass frequency band of said filter on the basis of the frequency band of the response signal from a contrast medium injected to said organism, and a control section for controlling the operation of said filter in the set pass band, wherein said transmitting section has means for transmitting an ultrasonic beam plural times at specific time intervals in the same direction, and means for constructing the continuous ultrasonic signal of each beam by the connection of waveforms of different frequencies and for generating the ultrasonic signals of the beams so as to be mutually asymmetrical with respect to polarity inversion, and said receiving section phase-processes and adds together the response signals of those ultrasonic signals of each beam which are continuous, and extracts said specific frequency component from the added signal using said filter.

11. The ultrasonic enhancement-contrast imager according to claim 10, wherein the pass band of said filter has an upper limit which is less than the high frequency limit of the frequency characteristics of the ultrasonic probe.

12. The ultrasonic enhancement-contrast imager according to claim 10, wherein the pass band of said filter has substantially a frequency band of a response signal of the contrast medium.

13. The ultrasonic enhancement-contrast imager according to claim 10, wherein the pass band of the filter is changed over time in accordance with a depth of the response signal.

14. An ultrasonic enhanced-contrast imager according to claim 13, wherein the pass band of said filter includes a second harmonic frequency for a shallow region and excludes a second harmonic frequency for a deep region.

15. The ultrasonic enhanced-contrast imager according to claim 10, wherein the pass band of the filter is changed over time in accordance with the time that has passed since the injection of the contrast medium.

16. An ultrasonic enhanced-contrast imager according to claim 15, wherein the pass band of the filter includes a second harmonic frequency for an initial time phase after the injection and excludes the second harmonic frequency for a later time phase after the injection.

17. An ultrasonic enhanced-contrast imager for enabling enhancement of an image when utilizing a contrast medium, characterized in that it comprises an ultrasonic probe for transmitting an ultrasonic wave to an organism which is reflected from the organism back to the ultrasonic probe, a transmitting section for transmitting an ultrasonic signal to the ultrasonic probe, and a receiving section for processing a response signal ultrasonic wave received by said ultrasonic probe, wherein said transmitting section has means for transmitting ultrasonic beams M (a natural number $\geq 2$) times at specific time intervals in the same direction, and the ultrasonic signal of each beam is constructed by the connection of waveforms of different frequency, and the signals are transmitted so as to be mutually asymmetrical with respect to polarity inversion, and said receiving section has means for phase-processing the response signals of the ultrasonic signals of said plural (M) transmissions, and means for attenuating the response signal from said tissue by adding or subtracting the phase-processed response signals.

18. The ultrasonic enhanced-contrast imager according to claim 17, wherein said receiving section has a filter for extracting a specific frequency component from the attenuated response signal of said organic tissue, and the pass band of the filter is set to be from $0.8f_0$ to $1.8f_0$, with said average frequency $f_0$ serving as a reference.

19. The ultrasonic enhanced-contrast imager according to claim 17, wherein said receiving section has a filter for extracting a specific frequency component from the attenuated response signal of said organic tissue, and the pass band of the filter is set to be from $1.2f_0$ to $1.8f_0$, with said average frequency $f_0$ serving as a reference.

20. The ultrasonic enhanced-contrast imager according to claim 17, wherein said receiving section has a filter for extracting a specific frequency component from the attenuated response signal of said organic tissue, and the pass band of the filter is changed over time in accordance with the depth of said response signal within a range of $0.8f_0$ to $1.8f_0$, with said average frequency $f_0$ serving as a reference.

21. An ultrasonic enhanced-contrast imager for enabling enhancement of an image when utilizing a contrast medium, characterized in that it comprises an ultrasonic probe for transmitting an ultrasonic wave to an organism which is reflected from the organism back to the ultrasonic probe, a transmitting section for transmitting an ultrasonic signal to the ultrasonic probe, and a receiving section for processing a response signal ultrasonic wave received by said ultrasonic probe, wherein said transmitting section has means for transmitting an ultrasonic beam M (a natural number $\geq 2$) times at specific time intervals in the same direction, and the ultrasonic signal of each transmission is formed by connecting N unit waveforms respectively having frequencies f1, f2, . . . , fn, fN (N is a natural number $\geq 2$), and a frequency distribution width $\Delta f$ of said f1 to fN is set within a range of $0.0f_0$ to $0.4f_0$, where $f_0$ is the average frequency of said signals from f1 to fN, and the ultrasonic signals of each transmission are transmitted so as to be mutually asymmetrical with respect to polarity inversion, and said receiving section has means for phasing-processing the response signals of the ultrasonic signals of said M transmissions, and means for attenuating the response signal of tissue of said organism by adding or subtracting the phase-processed response signals.

22. The ultrasonic enhanced-contrast imager according to claim 21, wherein said waveform of each time is represented by a code $f(A, \theta)$ prescribing a frequency f, an amplitude A and a starting phase, and comprises a first waveform formed by connecting the N-unit waveforms setting frequencies so that $f1(A1, \theta 1) < f2(A2, \theta 2) < \ldots < fn(An, \theta n) < \ldots < fN(AN, \theta N)$, setting the amplitude to be $A1=A2= \ldots =An = \ldots = AN$, and setting the starting phase to be $\theta 1=\theta 2= \ldots = \theta n= \ldots =\theta N=180°$, and also comprises a second waveform formed by connecting the N-unit waveforms setting frequencies so that $f1'(A1', \theta 1')>f2'(A2', \theta 2')> \ldots >fn'(An', \theta n')> \ldots >fN'(AN', \theta N')$, setting the amplitude to be $A1'=A2'= \ldots =An'= \ldots =AN'$ and setting the starting phase to be $\theta 1'=\theta 2'= \ldots =\theta n'= \ldots =\theta N'=0°$.

23. The ultrasonic enhanced-contrast imager according to claim 22, wherein frequency distribution widths $\Delta f$ and $\Delta f'$ of said f1 to fN and said f1' to fN' are respectively changed over time within a range of $0.0f_0$ to $0.4f_0$ in accordance with the depth of an ultrasonic irradiating focus.

24. The ultrasonic enhanced-contrast imager according to claim 23, wherein the frequency distribution widths $\Delta f$ and $\Delta f'$ of said f1 to fN and said f1' to fN' are set to $0.0f_0$ within a predetermined time after injection of the contrast medium, and are changed over time within the range of $0.0f_0$ to $0.4f_0$ after the predetermined time has passed.

25. The ultrasonic enhanced-contrast imager according to claim 21, wherein frequency distribution widths $\Delta f$ and $\Delta f'$ of said f1 to fN and said f1' to fN' are respectively changed over time within a range of $0.0f_0$ to $0.4f_0$ in accordance with the depth of ultrasonic irradiating focus.

26. The ultrasonic enhanced-contrast imager according to claim 21, wherein the frequency distribution widths $\Delta f$ and $\Delta f'$ of said f1 to fN and said f1' to fN' are set to $0.0f_0$ within a predetermined time after injection of the contrast medium, and are changed over time within the range of $0.0f_0$ to $0.4f_0$ after the predetermined time has passed.

27. An ultrasonic enhanced-contrast imager for enabling enhancement of an image when utilizing a contrast medium, characterized in that it comprises an ultrasonic probe for transmitting an ultrasonic wave to an organism which is reflected from the organism back to the ultrasonic probe, a transmitting section for transmitting an ultrasonic signal to the ultrasonic probe, and a receiving section for processing a response signal of the ultrasonic wave received by said ultrasonic probe, wherein said transmitting section has means for transmitting an ultrasonic beam M (a natural number $\geq 2$) times at specific time intervals in the same direction, and the ultrasonic signal of each transmission is constructed by the connection of waveforms of different frequencies, and at least the amplitude of its initial unit waveform is greater than the amplitude of the continuous unit waveform group, and the ultrasonic signals of each transmission are set so as to be mutually asymmetrical with respect to polarity inversion and time axis inversion, and said receiving section has means for phase-processing the response signals of the ultrasonic signals of said M transmissions, and means for attenuating the response signal of said organic tissue by adding or subtracting the phase-processed response signals.

28. The ultrasonic enhanced-contrast imager according to claim 27, wherein at least one of the following: frequency distribution widths $\Delta f$ and $\Delta f'$, amplitude distribution widths $\Delta A$ and $\Delta A'$ and amplitude weight (A/A') of the ultrasonic signal of each transmission, is changed over time in said transmitting section in accordance with the depth of the ultrasonic irradiating focus, or the time that has passed since the injection of a contrast medium.

29. The ultrasonic enhanced-contrast imager according to claim 27, wherein said waveforms of different frequencies are cycle waveforms whose polarities are alternately inverted and whose frequencies are the same.

30. The ultrasonic enhanced-contrast imager according to claim 27, wherein said waveform of each time is represented by a code $f(A, \theta)$ prescribing a frequency f, an amplitude A and a starting phase $\theta$, and comprises a first waveform formed by connecting N unit waveforms setting the frequencies so that $f1(A1, \theta 1)<f2(A2, \theta 2)< \ldots <fn(An, \theta n)< \ldots <fN(AN, \theta N)$, setting the amplitude to be $A1=A2= \ldots =An= \ldots =AN$, and setting the starting phase to be $\theta 1=\theta 2= \ldots =\theta n= \ldots =\theta N=180°$, and also comprises a second waveform formed by connecting N unit waveforms setting the frequencies so that $f1'(A1', \theta 1')>f2'(A2', \theta 2')> \ldots >fn'(An', \theta n')> \ldots >fN'(AN', \theta N')$, setting the amplitude to so that $A1'>A2'> \ldots >An'> \ldots >AN'$, and setting the starting phase to be $\theta 1'=\theta 2'= \ldots =\theta n'= \ldots \theta N'=0°$.

31. The ultrasonic enhanced-contrast imager according to claim 27, wherein said receiving section has a filter for extracting a specific frequency component from the attenuated response signal from tissue, and the pass band of the filter is set to be from $0.8f_0$ to $1.8f_0$, where said average frequency $f_0$ serves as a reference.

32. The ultrasonic enhanced-contrast imager according to claim 27, wherein said receiving section has a filter for extracting a specific frequency component from the attenuated response signal from tissue, and the pass band of the filter is set to be from $1.2f_0$ to $1.8f_0$, with said average frequency $f_0$ serving as a reference.

33. The ultrasonic enhanced-contrast imager according to claim 27, wherein said receiving section has a filter for extracting a specific frequency component from the attenuated response signal from tissue, and the pass band of the filter is changed over time in accordance with the depth of said response signal within a range from $0.8f_0$ to $1.8f_0$, with said average frequency $f_0$ serving as a reference.

34. An ultrasonic enhanced-contrast imager for enabling enhancement of an image when utilizing a contrast medium, characterized in that it comprises an ultrasonic probe for transmitting an ultrasonic wave to an organism which is reflected from the organism back to the ultrasonic probe, a transmitting section for transmitting an ultrasonic signal to the ultrasonic probe, and a receiving section for processing a response signal of the ultrasonic wave received by said ultrasonic probe, wherein said transmitting section has means for transmitting an ultrasonic beam M (a natural number $\geq 2$) times at a time interval in the same direction, and the ultrasonic signal of each transmission is formed by connecting N unit waveforms respectively having frequencies f1, f2, . . . fn, . . . fN (N is a natural number$\geq 2$), and the frequency distribution width $\Delta f$ of said f1 through fN is set within a range of $0.0f_0$ to $0.4f_0$ where f0 is the average of said frequencies f1 through fN, and at least the amplitude of its initial unit waveform is greater than the amplitude of the continuous unit waveform group, and the ultrasonic signals of each transmission are set so as to be mutually asymmetrical with respect to polarity inversion, and said receiving section has means for phase-processing the response signals of the ultrasonic signals of said M transmissions, and means for attenuating the response signal from tissue of said organism by adding or subtracting the phase-processed response signals.

35. An ultrasonic enhanced-contrast imager for enabling enhancement of an image when utilizing a contrast medium, characterized in that it comprises an ultrasonic probe for transmitting an ultrasonic wave to an organism which is reflected from the organism back to the ultrasonic probe, a transmitting section for transmitting an ultrasonic signal to the ultrasonic probe, and a receiving section for processing a response signal ultrasonic wave received by said ultrasonic probe, wherein said transmitting section has means for transmitting an ultrasonic beam M (a natural number $\geq 2$) times at specific time intervals in the same direction, and the ultrasonic signal of each transmission comprises half wave groups having different frequency components, and at least the amplitude of each signal's first half wave is greater than the amplitude of the half wave group connected to this first half wave, and these half wave groups are set so as to be mutually asymmetrical with respect to polarity and a time axis, and said receiving section has means for phase-processing the response signals to the ultrasonic signals of said M transmissions, and means for attenuating the response signal of said organic tissue by adding or subtracting the phase-processed response signals.

36. An ultrasonic enhanced-contrast imaging method for enabling enhancement of an image when utilizing a contrast medium, characterized in that it comprises a transmitting process for transmitting an ultrasonic signal to an ultrasonic probe for transmitting an ultrasonic wave to an organism which is reflected from the organism back to the ultrasonic probe, a receiving process for processing a response signal ultrasonic wave received by said ultrasonic probe, a filter process for extracting a specific frequency component from the processed response signal, a setting process for setting a width of a pass frequency band of said filter so as to enable discrimination of a response signal from a contrast medium injected to the organism with respect to a response signal from a tissue of the organism, and a control process for controlling the operation of said filter in the set pass band, wherein the pass band of said filter is set to be in a range from $0.8f_0$ to $2.5f_0$ in said setting process where, $f_0$ is the average frequency of said ultrasonic signals given to said ultrasonic probe.

37. The ultrasonic enhanced-contrast imaging method according to claim 36, wherein the pass band of said filter is set to be in the range from $0.8f_0$ to $1.8f_0$ in said setting process.

38. The ultrasonic enhanced-contrast imaging method according to claim 36, wherein the pass band of said filter is set to be in the range from $1.2f_0$ to $1.8f_0$ in said setting process.

39. The ultrasonic enhanced-contrast imaging method according to claim 36, wherein said ultrasonic signal having plural frequency components is sent to said ultrasonic probe in said transmitting section.

40. The ultrasonic enhanced-contrast imaging method according to claim 39, wherein said ultrasonic signal has a waveform formed by connecting waveforms of different frequencies.

41. The ultrasonic enhanced-contrast imaging method for enabling enhancement of an image when utilizing a contrast medium, characterized in that it comprises an ultrasonic probe for transmitting an ultrasonic wave to an organism and for receiving an ultrasonic wave from the organism, a transmitting section for transmitting an ultrasonic signal to the ultrasonic probe, a receiving section for processing a response signal ultrasonic wave received by said ultrasonic probe, a filter for extracting a specific frequency component from the processed response signal, a setting control section for setting the pass frequency band of said filter on the basis of the frequency band of the response signal from a contrast medium injected to said organism, and a control section for controlling the operation of said filter in the set pass band, which has a process for transmitting an ultrasonic beam plural times at specific time intervals in the same direction, and a process for constructing the ultrasonic signal of each transmission by the connection of waveforms of a different frequencies, and generating the ultrasonic signals of each transmission so as to be mutually asymmetrical with respect to polarity inversion, and said receiving process is set so as to add the response signals to those ultrasonic signals of each transmission which are continuous after phase-processing the response signals, and extract said specific frequency component from the added signal by said filter.

42. An ultrasonic enhanced-contrast imaging method for enabling enhancement of an image when utilizing a contrast medium, characterized in that it comprises a transmitting process for sending an ultrasonic signal to an ultrasonic probe for transmitting an ultrasonic wave to an organism which is reflected from the organism back to the ultrasonic probe, and a receiving process for processing a response signal ultrasonic wave received by said ultrasonic probe, wherein said transmitting process has a process for transmitting an ultrasonic beam M (a natural number $\geq 2$) times at specific time intervals in the same direction, and the ultrasonic signal of each transmission is constructed by the connection of waveforms of different frequencies, which are transmitted so as to be mutually asymmetrical with respect to polarity inversion, and said receiving section has a process for phase-processing the response signals to the ultrasonic signals of said M transmissions, and a process for attenuating the response signal of tissue of said organism by adding or subtracting the phased and processed response signals.

43. The ultrasonic enhanced-contrast imaging method according to claim 42, wherein said receiving process has a filter process for extracting a specific frequency component from the attenuated response signal of tissue, and the pass band of the filter is set to be from $0.8f_0$ to $1.8f_0$, with said average frequency $f_0$ serving as a reference.

44. The ultrasonic enhanced-contrast imaging method according to claim 42, wherein said receiving process has a filter process for extracting a specific frequency component from the attenuated response signal of tissue, and the pass band of the filter is set to be from $1.2f_0$ to $1.8f_0$, with said average frequency $f_0$ serving as a reference.

45. The ultrasonic enhanced-contrast imaging method according to claim 42, wherein said receiving process has a filter process for extracting a specific frequency component from the attenuated response signal of tissue, and the pass band of the filter is changed over time in accordance with the depth of said response signal within a range of from $0.8f_0$ to $1.8f_0$, with said average frequency $f_0$ serving as a reference.

46. An ultrasonic enhanced-contrast imaging method for enabling enhancement of an image when utilizing a contrast medium, characterized in that it is executed by arranging an ultrasonic probe for transmitting an ultrasonic wave to an organism which is reflected from the organism back to the ultrasonic probe, a transmitting section for transmitting an ultrasonic signal to the ultrasonic probe, and a receiving section for processing a response signal ultrasonic wave received by said ultrasonic probe, wherein said transmitting section has means for transmitting an ultrasonic beam M (a natural number $\geq 2$) times at specific time intervals in the same direction, and the ultrasonic signal of each transmission is formed by connecting unit waveforms respectively having frequencies f1, f2, . . . , fn, . . . , fN (N is a natural number $\geq 2$), and a frequency distribution width $\Delta f$ of said f1 through fN is set within a range of $0.0f_0$ to $0.4f_0$ where f0 is the average frequency of said f1 through fN, and the ultrasonic signals of each transmission is transmitted so as to be mutually asymmetrical with respect to polarity inversion, and said receiving section has means for phase-processing the response signals of the ultrasonic signals of said M transmissions, and means for attenuating the response signal of said organic tissue by adding or subtracting the phase-processed response signals.

47. The ultrasonic enhanced-contrast imaging method according to claim 46, wherein said waveform of each transmission is represented by a code f(A, θ) prescribing a frequency f, an amplitude A and a starting phase θ, and comprises a first waveform formed by connecting N unit waveforms setting the frequencies so that f1(A1, θ1)<f2(A2, θ2)< . . . <fn(An, θn)< . . . <fN(AN, θN setting the amplitude so that A1=A2= . . . =An= . . . =AN and setting the starting phase to be θ1=θ2= . . . =θn= . . . =θN=180°, and also comprises a second waveform formed by connecting N unit waveforms setting the frequencies so that f1'(A1', θ1')>f2' (A2', θ2')> . . . >fn'(An', θn')> . . . >fN'(AN', θN'), setting the amplitude so that A1'=A2'= . . . =An'= . . . =AN' and setting the starting phase to be θ1'=θ2'= . . . =θn'= . . . =θN'=0°.

48. The ultrasonic enhanced-contrast imaging method according to claim 46, wherein frequency distribution widths $\Delta f$ and $\Delta f'$ of said f1 to fN and said f1' to fN' are respectively changed over time within a range of $0.0f_0$ to $0.4f_0$ in accordance with the depth of an ultrasonic irradiating focus.

49. The ultrasonic enhanced-contrast imaging method according to claim 48, wherein the frequency distribution widths $\Delta f$ and $\Delta f'$ of said f1 to fN and said f1' to fN' are set to $0.0f_0$ within a predetermined time after injection of the contrast medium, and are changed over time within the range from $0.0f_0$ to $0.4f_0$ after the predetermined time has passed.

50. The ultrasonic enhanced-contrast imaging method according to claim 46, wherein frequency distribution widths $\Delta f$ and $\Delta f'$ of said f1 to fN and said f1' to fN' are respectively changed over time within a range of $0.0f_0$ to $0.4f_0$ in accordance with the depth of the ultrasonic irradiating focus.

51. The ultrasonic enhanced-contrast imaging method according to claim 46, wherein the frequency distribution widths $\Delta f$ and $\Delta f'$ of said frequencies of f1 through fN and f1' through fN' are set to be $0.0f_0$ within a predetermined time after injection of the contrast medium, and are changed over time within the range of $0.0f_0$ to $0.4f_0$ after the predetermined time has passed.

52. An ultrasonic enhanced-contrast imaging method for enabling enhancement of an image when utilizing a contrast medium, which comprises a transmitting process for transmitting an ultrasonic signal to an ultrasonic probe for transmitting an ultrasonic wave to an organism which is reflected from the organism back to the ultrasonic probe, and a receiving process for processing a response signal ultrasonic wave received by said ultrasonic probe, wherein said transmitting process has a process for transmitting an ultrasonic beam M (a natural number $\geq 2$) times at specific time intervals in the same direction, and the ultrasonic signal of each transmission is constructed by the connection of a waveform of a different frequency, and at least the amplitude of its initial unit waveform is greater than the amplitude of the continuous group of unit waveforms, and the ultrasonic signals of each transmission are set so as to be mutually asymmetrical with respect to polarity inversion and time axis inversion, and said receiving process has a process for phase-processing the response signals of the ultrasonic signals of said M transmissions, and a process for attenuating the response signal from tissue of said organism by adding or subtracting the phased and processed response signals.

53. The ultrasonic enhanced-contrast imaging method according to claim 52, wherein at least one of the following values: frequency distribution widths $\Delta f$ and $\Delta f'$, amplitude distribution widths $\Delta A$ and $\Delta A'$, and amplitude weight (A/A') of the ultrasonic signal of each transmission in said transmitting section, is changed over time in accordance with the depth of the ultrasonic irradiating focus, or the time which has passed since the injection of a contrast medium.

54. The ultrasonic enhanced-contrast imaging method according to claim 52, wherein said waveforms of different frequencies are cycle waveforms whose polarities are alternately inverted and whose frequencies are the same.

55. The ultrasonic enhanced-contrast imaging method according to claim 52, wherein said waveform of each transmission is represented by a code f(A, θ) prescribing a frequency f, an amplitude A and a starting phase θ, and comprises a first waveform formed by connecting N unit waveforms setting the frequencies so that f1(A1, θ1)<f2(A2, θ2)< . . . <fn(An, θn)< . . . <fN(AN, θN), setting the amplitude to be A1=A2= . . . =An= . . . =AN and setting the starting phase to be θ1=θ2= . . . =θn= . . . =θN=180°, and also comprises a second waveform formed by continuing the N-unit waveforms of f1'(A1', θ1')>f2'(A2', θ2')> . . . >fn' (An', θn')> . . . >fN'(AN', θN'), setting the amplitude to so that A1'>A2'> . . . >An'> . . . >AN' and the starting phase to θ1'=θ2'= . . . =θn'= . . . =θN'=0°.

56. The ultrasonic enhanced-contrast imaging method according to claim 52, wherein said receiving section has a filter for extracting a specific frequency component from the attenuated response signal of tissue, and the pass band of the filter is set to be from $0.8f_0$ to $1.8f_0$, with said average frequency $f_0$ serving as a reference.

57. The ultrasonic enhanced-contrast imaging method according to claim 52, wherein said receiving section has a filter for extracting a specific frequency component from the attenuated response signal of tissue, and the pass band of the filter is set to be from $1.2f_0$ to $1.8f_0$, with said average frequency $f_0$ serving as a reference.

58. The ultrasonic enhanced-contrast imaging method according to claim 52, wherein said receiving section has a filter for extracting a specific frequency component from the attenuated response signal of tissue, and the pass band of the filter is changed over time in accordance with the depth of said response signal within a range from $0.8f_0$ to $1.8f_0$, with said average frequency $f_0$ serving as a reference.

59. An ultrasonic enhanced-contrast imaging method for enabling enhancement of an image when utilizing a contrast medium, characterized in that it comprises a transmitting process for transmitting an ultrasonic signal to an ultrasonic probe for transmitting an ultrasonic wave to an organism which reflects an ultrasonic wave back to the ultrasonic probe, and a receiving process for processing a response signal ultrasonic wave received by said ultrasonic probe, wherein said transmitting process has means for transmitting an ultrasonic beam M (a natural number $\geq 2$) times at specific time intervals in the same direction, and the ultrasonic signal of each transmission is formed by connecting N unit waveforms respectively having frequencies f1, f2, ..., fn, ..., fN (N is a natural number $\geq 2$), and a frequency distribution width $\Delta f$ of said f1 through fN is set within a range from $0.0f_0$ to $0.4f_0$ where $f_0$ is the average frequency of said f1 through fN, and at least the amplitude of its initial unit waveform is greater than the amplitude of the continuous group of unit waveforms, and the ultrasonic signal of each transmission are set so as to be mutually asymmetrical with respect to polarity inversion, and said receiving process has a process for phase-processing the response signals of the ultrasonic signals of said M times, and a process for attenuating the response signal from tissue of said organism by adding or subtracting the phase-processed response signals.

60. An ultrasonic enhanced-contrast imaging method for enabling enhancement of an image when utilizing a contrast medium, characterized in that it comprises a transmitting process for transmitting an ultrasonic signal to an ultrasonic probe for transmitting an ultrasonic wave to an organism which is reflected back to the ultrasonic probe, and a receiving process for processing a response signal ultrasonic wave received by said ultrasonic probe, wherein said transmitting process has a process for transmitting an ultrasonic beam M (natural number $\geq 2$) times at specific time intervals in the same direction, and the ultrasonic signal of each transmission comprises a half wave group having different frequency components, and at least the amplitude of its first half wave is greater than the amplitude of the half wave group connected to this first half wave, and the half wave groups are set so as to be mutually asymmetrical with respect to polarity and time axis, and said receiving process has a process for phase-processing the response signals of the ultrasonic signals of said M times, and a process for attenuating the response signal from tissue of said organism by adding or subtracting the phase-processed response signals.

61. An ultrasonic enhanced-contrast imager for enabling enhancement of an image when utilizing a contrast medium, characterized in that it comprises an ultrasonic probe for transmitting an ultrasonic wave to an organism and for receiving an ultrasonic wave from the organism, a transmitting section for transmitting an ultrasonic signal to the ultrasonic probe, a receiving section for processing a response signal ultrasonic wave received by said ultrasonic probe, a filter for extracting a specific frequency component from the processed response signal, a setting control section for setting a width of the pass frequency band of said filter so as to enable discrimination of a response signal from a contrast medium injected to the organism with respect to a response signal from a tissue of the organism, and a control section for controlling the operation of said filter in the set pass band, wherein the pass band of said filter has an upper limit which is less than a high frequency limit of the frequency characteristics of the ultrasonic probe.

62. An ultrasonic enhanced-contrast imager for enabling enhancement of an image when utilizing a contrast medium, characterized in that it comprises an ultrasonic probe for transmitting an ultrasonic wave to an organism and for receiving an ultrasonic wave from the organism, a transmitting section for transmitting an ultrasonic signal to the ultrasonic probe, a receiving section for processing a response signal ultrasonic wave received by said ultrasonic probe, a filter for extracting a specific frequency component from the processed response signal, a setting control section for setting a width of the pass frequency band of said filter so as to enable discrimination of a response signal from a contrast medium injected to the organism with respect to a response signal from a tissue of the organism, and a control section for controlling the operation of said filter in the set pass band, wherein the pass band of said filter has substantially a frequency band of the response signal of the contrast medium.

* * * * *